(12) United States Patent
Parsons

(10) Patent No.: US 10,890,590 B2
(45) Date of Patent: Jan. 12, 2021

(54) DIAGNOSTIC DEVICES AND METHODS

(71) Applicant: Ellume Limited, Queensland (AU)

(72) Inventor: Sean Andrew Parsons, East Brisbane (AU)

(73) Assignee: Ellume Limited, Queensland (AU)

( * ) Notice: Subject to any disclaimer, the term of this patent is extended or adjusted under 35 U.S.C. 154(b) by 400 days.

(21) Appl. No.: 14/672,789

(22) Filed: Mar. 30, 2015

(65) Prior Publication Data

US 2015/0204891 A1    Jul. 23, 2015

Related U.S. Application Data

(63) Continuation-in-part of application No. 14/431,155, filed as application No. PCT/AU2013/001115 on Sep. 27, 2013, now abandoned.

(30) Foreign Application Priority Data

Sep. 27, 2012    (AU) ............................... 2012904238

(51) Int. Cl.
    *G01N 33/76* (2006.01)
(52) U.S. Cl.
    CPC ......... *G01N 33/76* (2013.01); *G01N 2333/59* (2013.01)
(58) Field of Classification Search
    None
    See application file for complete search history.

(56) References Cited

U.S. PATENT DOCUMENTS

| | | | |
|---|---|---|---|
| 4,338,305 A | 7/1982 | Corbin | |
| 4,999,287 A | 3/1991 | Allen et al. | |
| 5,418,136 A | 5/1995 | Miller et al. | |
| 5,503,985 A | 4/1996 | Cathey et al. | |
| 5,525,520 A | 6/1996 | Dinh | |
| 5,629,214 A | 5/1997 | Crosby | |
| 5,783,399 A | 7/1998 | Childs et al. | |
| 5,786,220 A | 7/1998 | Pronovost et al. | |
| 5,824,268 A | 10/1998 | Bernstein et al. | |
| 5,902,982 A | 5/1999 | Lappe | |
| 5,939,252 A | 8/1999 | Lennon et al. | |
| 5,942,407 A | 8/1999 | Liotta et al. | |
| 5,998,220 A | 12/1999 | Chandler | |
| 6,033,627 A | 3/2000 | Sheilds et al. | |
| 6,136,610 A * | 10/2000 | Polito ............. | G01N 33/54386 422/82.05 |
| 6,248,294 B1 | 6/2001 | Nason | |
| 6,267,722 B1 | 7/2001 | Anderson et al. | |
| 6,319,665 B1 | 11/2001 | Zwanziger et al. | |
| 6,319,965 B1 | 11/2001 | Kamohara et al. | |
| 6,352,862 B1 | 3/2002 | Davis et al. | |
| 6,365,417 B1 | 4/2002 | Fleming et al. | |
| 6,454,705 B1 | 9/2002 | Cosentino et al. | |
| 6,549,275 B1 | 4/2003 | Cabuz et al. | |
| 6,627,459 B1 | 9/2003 | Tung et al. | |
| 6,656,745 B1 | 12/2003 | Cole | |
| 6,764,849 B2 | 7/2004 | Small et al. | |
| 6,886,864 B2 | 5/2005 | Nelson et al. | |
| 6,991,940 B2 | 1/2006 | Carroll et al. | |
| 6,998,273 B1 | 2/2006 | Fleming et al. | |
| 7,044,919 B1 | 5/2006 | Catt et al. | |
| 7,070,920 B2 | 7/2006 | Spivey et al. | |
| 7,214,542 B2 | 5/2007 | Hutchinson | |
| 7,220,597 B2 | 5/2007 | Zin et al. | |
| 7,279,136 B2 | 10/2007 | Takeuchi et al. | |
| 7,280,201 B2 | 10/2007 | Helbing | |
| 7,300,800 B2 | 11/2007 | Bell et al. | |
| 7,315,378 B2 | 1/2008 | Phelan et al. | |
| 7,459,314 B2 | 12/2008 | Guo et al. | |
| 7,460,222 B2 | 12/2008 | Kalveram et al. | |
| 7,486,396 B2 | 2/2009 | Oldham et al. | |
| 7,488,450 B2 | 2/2009 | Matusewicz et al. | |
| 7,489,403 B1 | 2/2009 | Lin et al. | |

(Continued)

FOREIGN PATENT DOCUMENTS

| | | |
|---|---|---|
| CA | 2496986 A1 | 10/2005 |
| CA | 2802318 A1 | 1/2012 |

(Continued)

OTHER PUBLICATIONS

"Understanding Your Ovulation Cycle FemailFemale Menstrual Cycle Step by Step." The Fertility Realm online. Jul. 9, 2012. [http://www.thefertilityrealm.com/ovulation-cycle.html]. Internet Archive. [www.https://web.archive.org/web/20120709173120/http:www.thefertilityrealm.com/ovulation-cycle.html] Accessed Jan. 13, 2016. (4 pages).*
Extended European Search Report for European Application No. 14783290.1 dated Sep. 15, 2016, 7 pages.
Cook et al., Printed Circuit Board Tracking with RFID: Speed, Efficiency and Productivity Made Simple. Texas Instruments RFID White Paper. Feb. 2008; 9 pages.
Snyder, Diagnostic Considerations in the Measurement of Human Chorionic Gonadotropin in Aging Women. Clinical Chemistry. Aug. 11, 2005; 51(10):1830-35.

(Continued)

*Primary Examiner* — Ellen J Marcsisin
(74) *Attorney, Agent, or Firm* — Michael B. Rubin; Bozicevic, Field & Francis LLP

(57) ABSTRACT

Apparatus is disclosed for identifying at least a first target condition in a human or animal body. The apparatus comprises one or more test portions for identifying a first analyte in a biological sample from the body, the first analyte providing a marker of the first target condition, and a second analyte in the biological sample, the second analyte being different from the first analyte. The apparatus is configured to identify the first target condition in the body based on the identification of both the first and second analytes. In one embodiment, the first target condition is pregnancy, the first analyte is human chorionic gonadotropin (hCG) and the second analyte is luteinizing hormone (LH).

37 Claims, 14 Drawing Sheets

(56) References Cited

U.S. PATENT DOCUMENTS

| | | | |
|---|---|---|---|
| 7,553,453 B2 | 6/2009 | Gu et al. | |
| 7,616,315 B2 | 11/2009 | Sharrock et al. | |
| 7,651,851 B2 | 1/2010 | Clarke et al. | |
| 7,682,801 B2 | 3/2010 | Esfandiari | |
| 7,688,440 B2 | 3/2010 | Clarke et al. | |
| 7,740,801 B2 | 6/2010 | Saini et al. | |
| 7,763,454 B2 | 7/2010 | Nazareth et al. | |
| 7,803,322 B2 | 9/2010 | Borich et al. | |
| 7,815,854 B2 | 10/2010 | Cohen | |
| 7,879,597 B2 | 2/2011 | Esfandiari | |
| 7,879,624 B2 | 2/2011 | Sharrock | |
| 7,927,561 B2 | 4/2011 | Kirakossian et al. | |
| 7,941,376 B2 | 5/2011 | Peckover | |
| 8,003,060 B2 | 8/2011 | Cracauer et al. | |
| 8,018,593 B2 | 9/2011 | Tan et al. | |
| 8,030,091 B2 | 10/2011 | Jerome et al. | |
| 8,040,494 B2 | 10/2011 | Ermantraut et al. | |
| 8,093,057 B2 | 1/2012 | Choi et al. | |
| 8,101,431 B2 | 1/2012 | McDevitt et al. | |
| 8,105,552 B2 | 1/2012 | Xiao et al. | |
| 8,105,794 B2 | 1/2012 | Shaari | |
| 8,105,849 B2 | 1/2012 | McDevitt et al. | |
| 8,110,392 B2 | 2/2012 | Battrel et al. | |
| 8,128,871 B2 | 3/2012 | Petruno et al. | |
| 8,133,671 B2 | 3/2012 | Williams et al. | |
| 2001/0021536 A1 | 9/2001 | Lee | |
| 2002/0004246 A1 | 1/2002 | Daniels et al. | |
| 2002/0031839 A1 | 3/2002 | McNierney et al. | |
| 2002/0111741 A1 | 8/2002 | Abraham-Fuchs et al. | |
| 2003/0032199 A1 | 2/2003 | Meusel et al. | |
| 2003/0049175 A1 | 3/2003 | Buechler et al. | |
| 2003/0119030 A1 | 6/2003 | Zilber | |
| 2004/0019301 A1 | 1/2004 | Wong et al. | |
| 2004/0119591 A1 | 6/2004 | Peeters | |
| 2004/0151632 A1 | 8/2004 | Badley et al. | |
| 2005/0095697 A1 | 5/2005 | Bachur et al. | |
| 2005/0130120 A1 | 6/2005 | Lambotte et al. | |
| 2005/0136553 A1 | 6/2005 | Kaylor et al. | |
| 2005/0196318 A1 | 9/2005 | Matusewicz et al. | |
| 2005/0208593 A1 | 9/2005 | Vail et al. | |
| 2005/0221505 A1 | 10/2005 | Petruno et al. | |
| 2006/0019265 A1 | 1/2006 | Song et al. | |
| 2006/0019404 A1 | 1/2006 | Blatt et al. | |
| 2006/0025732 A1 | 2/2006 | Ying et al. | |
| 2006/0216832 A1 | 9/2006 | Nishikawa et al. | |
| 2006/0246513 A1 | 11/2006 | Bohannon | |
| 2006/0257992 A1 | 11/2006 | McDevitt et al. | |
| 2006/0263244 A1 | 11/2006 | Rannikko et al. | |
| 2007/0015285 A1 | 1/2007 | Catt et al. | |
| 2007/0020274 A1* | 1/2007 | Cole | C07K 16/26 424/155.1 |
| 2007/0031283 A1 | 2/2007 | Davis et al. | |
| 2007/0081920 A1 | 4/2007 | Murphy et al. | |
| 2007/0184495 A1 | 8/2007 | Shaari | |
| 2007/0231923 A1 | 10/2007 | Cumberland et al. | |
| 2007/0298436 A1 | 12/2007 | Lappe | |
| 2008/0102473 A1 | 5/2008 | Fouquet et al. | |
| 2008/0113391 A1 | 5/2008 | Gibbons et al. | |
| 2008/0113427 A1 | 5/2008 | Kikta | |
| 2008/0213920 A1 | 9/2008 | Nazareth et al. | |
| 2008/0311003 A1 | 12/2008 | Chiu | |
| 2009/0027501 A1 | 1/2009 | Elangovan et al. | |
| 2009/0035743 A1 | 2/2009 | Minter et al. | |
| 2009/0061507 A1 | 3/2009 | Ho | |
| 2009/0061534 A1 | 3/2009 | Sharrock | |
| 2009/0155811 A1 | 6/2009 | Natan et al. | |
| 2009/0192820 A1 | 7/2009 | Bodlaender et al. | |
| 2009/0196792 A1* | 8/2009 | Raj | G01N 33/558 422/400 |
| 2009/0197296 A1 | 8/2009 | Martin et al. | |
| 2009/0202388 A1 | 8/2009 | Matusewicz et al. | |
| 2009/0263905 A1 | 10/2009 | Scheuringer | |
| 2009/0280576 A1 | 11/2009 | Donati | |
| 2009/0298059 A1 | 12/2009 | Gumbrecht et al. | |
| 2009/0314946 A1 | 12/2009 | Song et al. | |
| 2010/0009430 A1 | 1/2010 | Wan et al. | |
| 2010/0055721 A1 | 3/2010 | Lambert et al. | |
| 2010/0087749 A1 | 4/2010 | Tovey | |
| 2010/0121156 A1 | 5/2010 | Yoo | |
| 2010/0135857 A1 | 6/2010 | Hunter et al. | |
| 2010/0176279 A1 | 7/2010 | Lai | |
| 2010/0239460 A1 | 9/2010 | Nazareth et al. | |
| 2010/0240149 A1 | 9/2010 | Nazareth et al. | |
| 2010/0248277 A1 | 9/2010 | Gibbons et al. | |
| 2010/0272635 A1 | 10/2010 | Rodems et al. | |
| 2010/0291588 A1 | 11/2010 | McDevitt et al. | |
| 2010/0304397 A1 | 12/2010 | Burns et al. | |
| 2011/0038767 A1 | 2/2011 | Baril | |
| 2011/0151584 A1 | 6/2011 | Esfandiari | |
| 2011/0178723 A1 | 7/2011 | Sharrock et al. | |
| 2011/0195441 A1 | 8/2011 | Hemker et al. | |
| 2011/0213564 A1 | 9/2011 | Henke | |
| 2011/0213579 A1 | 9/2011 | Henke | |
| 2011/0213619 A1 | 9/2011 | Henke | |
| 2011/0266462 A1 | 11/2011 | Doi | |
| 2011/0294199 A1 | 12/2011 | Bearinger et al. | |
| 2012/0015448 A1 | 1/2012 | Sharrock | |
| 2012/0096400 A1 | 4/2012 | Cho | |
| 2012/0129272 A1 | 5/2012 | Petruno et al. | |
| 2013/0065321 A1 | 3/2013 | Nazareth et al. | |
| 2013/0096400 A1 | 4/2013 | Dahl et al. | |
| 2013/0280795 A1 | 10/2013 | Dahl et al. | |
| 2014/0296667 A9 | 10/2014 | Dahl et al. | |
| 2015/0094227 A1 | 4/2015 | McCarthy et al. | |
| 2015/0241455 A1 | 8/2015 | Parsons | |

FOREIGN PATENT DOCUMENTS

| | | | |
|---|---|---|---|
| CN | 101137897 A | 3/2008 | |
| CN | 101551398 A | 10/2009 | |
| EP | 1051616 A2 | 11/2000 | |
| EP | 1484601 A2 | 12/2004 | |
| EP | 1918708 A2 | 5/2008 | |
| EP | 1718973 B1 | 9/2009 | |
| EP | 2385363 A2 | 11/2011 | |
| FR | 2929407 A1 | 10/2009 | |
| JP | H10-132817 | 5/1998 | |
| JP | H11-281645 A | 9/1999 | |
| JP | H11-281645 A | 10/1999 | |
| JP | 2002-510799 | 4/2002 | |
| JP | 3496154 B2 | 2/2004 | |
| JP | 2009/085839 A | 4/2009 | |
| WO | WO 95/16207 A1 | 6/1995 | |
| WO | WO 95/33996 A1 | 12/1995 | |
| WO | WO 96/34287 A1 | 10/1996 | |
| WO | WO 99/06827 A1 | 2/1999 | |
| WO | WO 99/56111 A1 | 11/1999 | |
| WO | WO 01/98783 A2 | 12/2001 | |
| WO | WO 02/088739 A1 | 11/2002 | |
| WO | WO 2004/003527 A1 | 1/2004 | |
| WO | WO 2005/031355 A1 | 4/2005 | |
| WO | 2005059547 | 6/2005 | |
| WO | WO 2005/075982 A2 | 8/2005 | |
| WO | WO 2005/084534 A1 | 9/2005 | |
| WO | WO 2005/111579 A1 | 11/2005 | |
| WO | WO 2006/091631 A2 | 8/2006 | |
| WO | WO 2006/099191 A2 | 9/2006 | |
| WO | WO-2006100415 A1 * | 9/2006 | ............ G01N 33/76 |
| WO | WO 2006/119203 A2 | 11/2006 | |
| WO | WO 2006/129761 A1 | 12/2006 | |
| WO | 2007049157 | 5/2007 | |
| WO | 2006100415 | 9/2007 | |
| WO | WO 2007/132375 A1 | 11/2007 | |
| WO | WO 2007/132376 A2 | 11/2007 | |
| WO | WO 2008/001279 A2 | 1/2008 | |
| WO | WO 2010/015843 A1 | 2/2010 | |
| WO | WO 2010/055308 A1 | 5/2010 | |
| WO | WO 2010/148252 A1 | 12/2010 | |
| WO | WO 2011/091473 A1 | 8/2011 | |
| WO | WO 2011/154918 A2 | 12/2011 | |
| WO | WO 2012/010454 A1 | 1/2012 | |
| WO | WO 2012/044530 A1 | 4/2012 | |
| WO | WO 2013/036913 A1 | 3/2013 | |
| WO | 2014047692 | 4/2014 | |

(56) References Cited

FOREIGN PATENT DOCUMENTS

| WO | WO 2014/085926 A1 | 6/2014 |
|---|---|---|
| WO | 2015049508 | 4/2015 |
| WO | 2015121661 | 8/2015 |

OTHER PUBLICATIONS

International Search Report and Written Opinion for Application No. PCT/AU2011/000085 dated May 18, 2011.

Patent Examination Report No. 2 for Australian Patent application No. 2013204428, dated Jan. 20, 2016 (7pgs.)

Liu et al., Disposable electrochemical immunosensor diagnosis device based on nanoparticle probe and immunochromatographic strip. Anal Chem. Oct. 2007;79(20):7644-53. Epub Sep. 19, 2007. PubMed PMID: 17877418.

Young et al., Development of an ultrarapid one-step fluorescence immunochromatographic assay system for the quantification of microcystins. Environ. Sci. Technol. May 2003; 37 (9):1899-904. PubMed PMID: 12775063.

International Search Report and Written Opinion for PCT/AU2013/001115, dated Dec. 17, 2013 (14 pages).

Adejuwon et al., Daily serum choriogonadotropin concentrations in early human gestation, Intl. J. Gynaecol. Obstet., 1984, pp. 125-129, vol. 22, International Federation of Gynaecology & Obstetrics, Ireland.

Cole et al., Background hCG in non-pregnant individuals: Need for more sensitive point-of-care and over-the-counter pregnancy tests, Clinical Biochemistry, 2009, pp. 168-175, vol. 42, Elsevier.

Cole et al., Normal Production of Human Chorionic Gonadotropin in Perimenopausal and Menopausal Women and After Oophorectomy, International Journal of Gynecological Cancer, Dec. 2009, pp. 1556-1559, vol. 19, No. 9, IGCS and ESGO.

Cole et al., Production of Human Chorionic Gonadotropin During the Normal Menstrual Cycle, The Journal of Reproductive Medicine, Apr. 2009, pp. 245-250, vol. 54, issue 4, Journal of Reproductive Medicine, Inc.

Corker et al., Hormonal patterns in conceptual cycles and early pregnancy, British Journal of Obstetrics and Gynaecology, Jun. 1976, pp. 489-494, vol. 83.

Gronowski et al., Use of Serum FSH to Identify Perimenopausal Women with Pituitary hCG, Clinical Chemistry, 2008, pp. 652-656, vol. 54, No. 4.

Jia et al., Luminescence Luteinizing Hormone/Choriogonadotropin (LH/CG) Bioassay: Measurement of Serum Bioactive LH/CG during Early Pregnancy in Human and Macaque, Biology of Reproduction, 1993, pp. 1310-1316, vol. 49.

Mishell, Jr. et al., Hormone Patterns in Early Human Gestation, Basic Life Sciences, pp. 371-384, vol. 4, Plenum Press, New York.

Mishell, Jr. et al., Serum gonadotropin and steroid patterns in early human gestation, American Journal of Obstetrics and Gynecology, 1973, pp. 631-642, vol. 1, C.V. Mosby, St. Louis, Missouri.

Rowe, An Array Immunosensor for Simultaneous Detection of Clinical Analytes, Anal. Chem., Jan. 15, 1999, pp. 433-439, vol. 71, No. 2.

Wide, Early Diagnosis of Pregnancy, The Lancet, Oct. 25, 1969, pp. 863-864.

Nilsson et al, (2001) "Immunological characterization of human luteinizing hormone with special regard to a common genetic variant"; Journal of Endocrinology, 168; pp. 107-116.

* cited by examiner

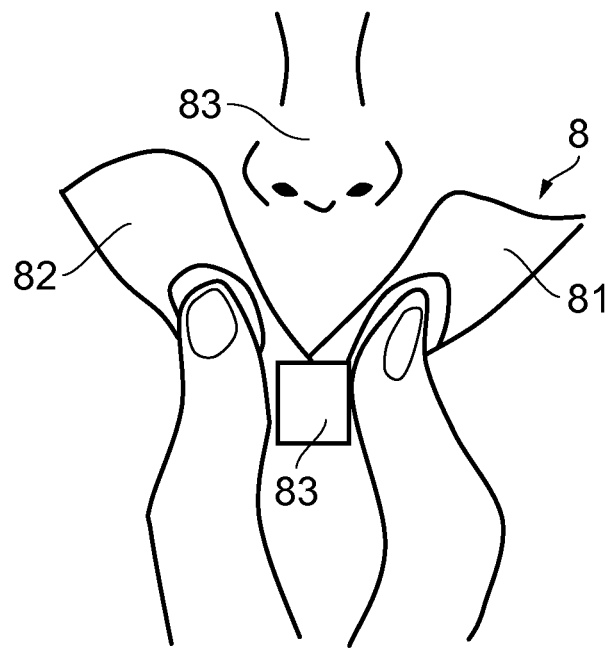
FIG. 10
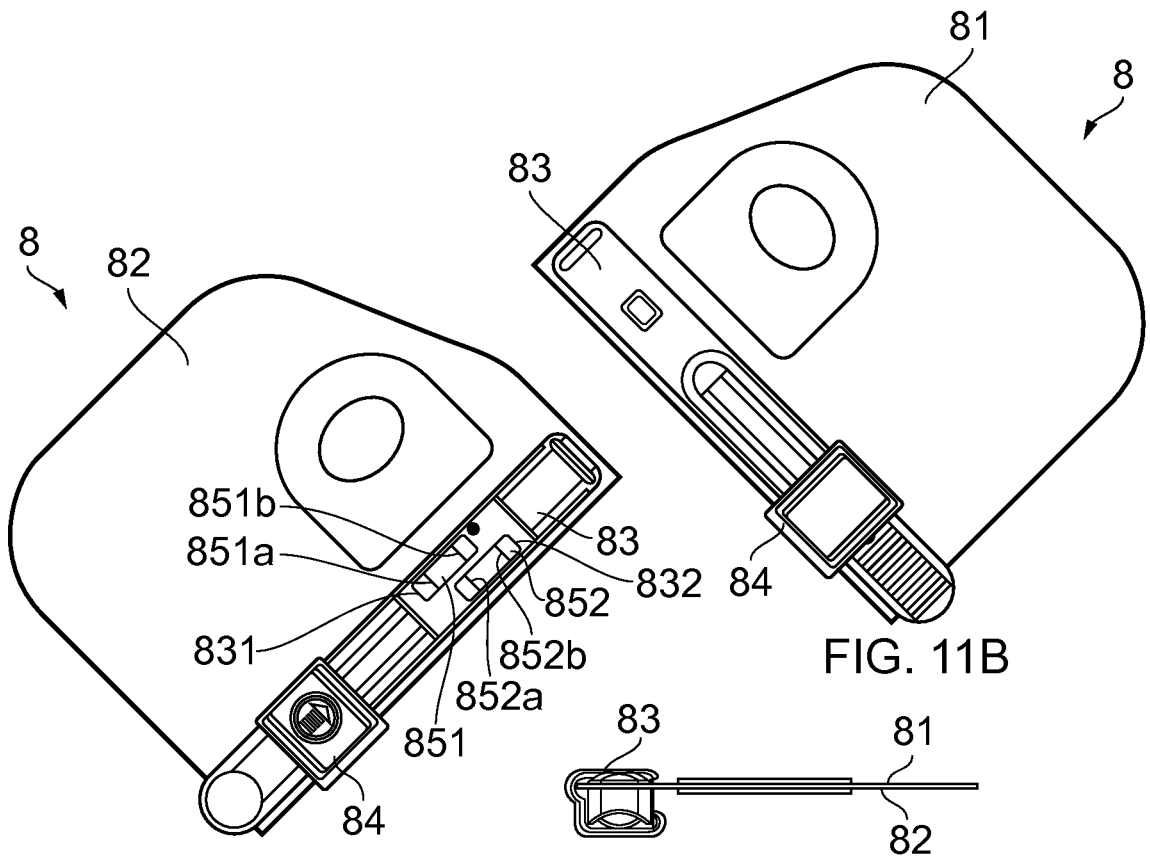
FIG. 11A
FIG. 11B
FIG. 11C

|  | | FALSE POSITIVE ||||||||
|  | | LH ||||||||
|  |  | <5.0 | <10.0 | <15.0 | <20.0 | <25.0 | <30.0 | <40.0 | Total |
| hCG | 1.0 | 0.07% | 0.23% | 0.53% | 0.72% | 1.10% | 1.38% | 1.89% | 8.22% |
|  | 1.1 | 0.06% | 0.18% | 0.34% | 0.49% | 0.76% | 0.96% | 1.33% | 6.65% |
|  | 1.2 | 0.05% | 0.14% | 0.25% | 0.34% | 0.53% | 0.70% | 0.95% | 5.29% |
|  | 1.3 | 0.02% | 0.07% | 0.14% | 0.19% | 0.35% | 0.47% | 0.68% | 4.21% |
|  | 1.4 | 0.01% | 0.06% | 0.08% | 0.13% | 0.26% | 0.35% | 0.53% | 3.49% |
|  | 1.5 | 0.00% | 0.05% | 0.06% | 0.09% | 0.19% | 0.27% | 0.42% | 2.91% |
|  | 1.6 | 0.00% | 0.04% | 0.05% | 0.06% | 0.15% | 0.20% | 0.34% | 2.53% |
|  | 1.7 | 0.00% | 0.04% | 0.05% | 0.06% | 0.14% | 0.19% | 0.32% | 2.21% |
|  | 1.8 | 0.00% | 0.04% | 0.05% | 0.06% | 0.14% | 0.19% | 0.32% | 2.02% |
|  | 1.9 | 0.00% | 0.04% | 0.05% | 0.06% | 0.12% | 0.18% | 0.29% | 1.90% |
|  | 2.0 | 0.00% | 0.04% | 0.05% | 0.06% | 0.11% | 0.17% | 0.27% | 1.69% |
|  | 2.5 | 0.00% | 0.03% | 0.03% | 0.05% | 0.07% | 0.11% | 0.19% | 1.20% |
|  | 3.0 | 0.00% | 0.01% | 0.01% | 0.01% | 0.03% | 0.06% | 0.13% | 0.91% |

Fig. 14C

DIAGNOSTIC DEVICES AND METHODS

CROSS-REFERENCE TO RELATED APPLICATIONS

The present application is a continuation-in-part of U.S. patent application Ser. No. 14/431,155, filed on Mar. 25, 2015, entitled Diagnostic Devices and Methods, which is a 35 U.S.C. 371 U.S. National Stage Application of International Patent Application No. PCT/AU2013/001115, filed on 27 Sep. 2013, which claims the benefit of priority from Australian Provisional Patent Application No 2012904238 filed on 27 Sep. 2012. The entire contents of each of these applications is incorporated herein by reference.

TECHNICAL FIELD

The present disclosure relates to devices and methods for identifying conditions in a human or animal body such as pregnancy.

BACKGROUND

There exist many types of diagnostic devices for identifying target medical conditions in a human or animal. Increasingly, these devices are being designed for home use. The devices analyse a biological sample from the human or animal, such as a urine sample, blood sample or otherwise, and identify an analyte in the sample that provides a marker for a target condition.

One of the most widely used and recognised diagnostic devices is the home pregnancy test, which commonly employs lateral flow technology and uses human chorionic gonadotropin (hCG) as a marker for pregnancy.

Diagnostic devices that allow highly accurate testing are clearly desirable. Many diagnostic devices provide for binary identification of the target condition, where it is determined only if the target condition is present (a positive result) or not present (a negative result). In these devices, accuracy is a function of the sensitivity of the device, which is its ability to detect true positive results, and the specificity of the device, which is its ability to detect true negative results. Increasing accuracy is particularly important for diagnostic devices used at home, where there can be no trained health professional to interpret identification results and the value of the results to the care of a patient.

The sensitivity of diagnostic devices increases when the devices are configured to detect smaller amounts of the marker analyte, yielding more true positive results. The increase is limited, however, by the increased susceptibility of the device to detecting background amounts of the marker analyte, which may be present naturally in the sample, for example, resulting in a greater number of false positive results. Generally, background production of the marker analyte therefore constitutes "physiological noise" and creates a limit to the usefulness in improvements to the sensitivity of certain diagnostic devices.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to an aspect of the present disclosure there is provided apparatus for identifying at least a first target condition in a human or animal body, the apparatus comprising:
one or more test portions for identifying:
a first analyte in a biological sample from the body, the first analyte providing a marker of the first target condition; and
a second analyte in the biological sample, the second analyte being different from the first analyte;
wherein the apparatus is configured to identify the first target condition in the body based on the identification of both the first and second analytes.

According to another aspect of the present disclosure there is provided a method for identifying a first target condition in a human or animal body, the method comprising:
identifying a first analyte in a biological sample from the body, the first analyte providing a marker of the first target condition; and
identifying a second analyte in the biological sample, the second analyte being different from the first analyte;
and identifying the first target condition in the body based on the identification of both the first and second analytes.

In the preceding and subsequent aspects, identifying the first and/or second analyte in the biological sample may comprise identifying that the first and/or second analyte is present or absent in the sample or identifying a level at which the first and/or second analyte is present in the sample. Similarly, identifying the first target condition may comprise identifying that the first target condition is present or absent in the body or identifying a level at which the first target condition is present in the body. Identification of the level of an analyte in the sample may include identification of an amount of the analyte in all or part of the sample provided. The amount may be determined in a number of ways, e.g. through extrapolation or direct measurement or otherwise, and/or expressed in a number of ways, e.g. as a density, a light intensity, a measure of power intensity or in IU/L, or otherwise.

The second analyte may provide a marker of a second condition of the body, which may be considered a non-target condition or a further target condition, and/or the second analyte may provide an indication of the quality or size of the sample or a component part of the sample.

A condition may be considered a "target condition" on the basis that the apparatus and method is adapted to provide information to the user in respect to identification of that condition, e.g. via a display or otherwise. A "target condition" may therefore be a condition about which the user of the apparatus is intending to discover information. On the other hand a "non-target condition" may be a condition about which the user of the apparatus has no direct interest. The device may be configured not to display information to the user about the non-target condition, for example.

The term "analyte" is used herein to define any compound or composition to be measured in a sample.

The apparatus disclosed herein may comprise any one or more capture agents capable of binding specifically to any one of more of the analytes in the sample. Any suitable capture agents may be used. For example, the capture agents may be any one of more agents that have the capacity to bind a relevant species to form a binding pair. Some examples of such binding pairs include, but are not limited to, an antibody (which term encompasses antigen-binding variants or fragments of antibodies, such as Fv, scFv, Fab, Fab1, F(ab')2, domain antibodies (dAbs), "minibodies" and the like, in addition to monoclonal and polyclonal antibodies) and an antigen (wherein the antigen may be, for example, a peptide sequence or a protein sequence); complementary nucleotide or peptide sequences; polymeric acids and bases; dyes and protein binders; peptides and protein binders; enzymes and cofactors, and ligand and receptor molecules, wherein the term receptor refers to any compound or composition capable of recognising a particular molecule configuration, such as an epitopic or determinant site. The capture agent can be an antibody or fragment thereof, which is capable of binding specifically to the analyte of interest.

The apparatus may be a device that operates as a single unit. The apparatus may be provided in the form of a hand-held device. The apparatus may be a single-use, disposable, device. Alternatively, the apparatus may be partly or entirely re-usable. While in some embodiments the apparatus may be implemented in a laboratory, the apparatus may designed as a 'point-of-care' device, for home use or use in a clinic, etc. The apparatus may provide a rapid-test device, with identification of target conditions being provided to the user relatively quickly, e.g., in under 10 minutes, 5 minutes or under 1 minute.

The one or more test portions may be configured for identifying one or more further analytes in the biological sample, e.g. a third analyte different from the first and second analytes. The further analytes may provide markers of further target or non-target conditions of the body and/or provide other indications such as an indication of the quality or size of the sample or a component part of the sample.

The present disclosure recognises that, while identifying the first analyte in the biological sample may provide a prima facie indication of the first target condition in the body, the degree to which the first analyte is present in the sample may have been affected by something other than the first target condition, such as a different condition and/or a quality or size of the sample or part thereof or otherwise. The degree to which it is affected can be correlated at least in part to the degree to which the second analyte is present in the sample. Accordingly, to reduce the possibility that an erroneous determination might be made about at least the first target condition, the apparatus and method can take into account identification of at least the second analyte when identifying the first target condition in consideration of the first analyte. The apparatus and method may therefore provide for a co-interpretation of the identification of the first and second analytes in order to identify at least the first target condition.

In one embodiment, the first target condition may be identified as being present in the body based on a determination that (i) the first analyte is present in the sample or present at a level above a threshold level in the sample, and (ii) the second analyte is absent from the sample or present at a level below a threshold level in the sample.

In another embodiment, the first target condition may be identified as being present in the body based on a determination that the first analyte is present at a level above a threshold level in the sample, wherein the threshold level is changed depending on the level of the second analyte present in the sample.

In one embodiment, the first target condition may be identified as being present in the body based on a determination that (i) the first analyte is absent from the sample or present at a level below a threshold level in the sample, and (ii) the second analyte is present in the sample or present at a level above a threshold level in the sample.

In another embodiment, the first target condition may be identified as being present in the body based on a determination that the first analyte is present at a level below a threshold level in the sample, wherein the threshold level is changed depending on the level of the second analyte present in the sample.

While in the above-described embodiments it is described that the presence, in particular, of the first target condition is identified based on certain criteria, in some embodiments the same criteria may be used to determine the level of a first target condition that is present in the body, or to determine the absence of a first target condition in the body. Furthermore, the apparatus and method may also be configured to determine if identification of the first target condition is not possible. For example, it may be determined that the level at which the second analyte is present in the sample renders any identification of the first target condition based on the first analyte unfeasible. Such a determination may result in a need to carry out identification of the first target condition using different apparatus or a different method, or to repeat the identification using the same apparatus or method immediately or at a later stage.

The apparatus and method may be used to identify a variety of different target conditions using a variety of different types of biological samples and a variety of different first and second analytes. Biological samples may include, for example, blood, serum, plasma, saliva, sputum, urine, ocular fluid, tears, semen, vaginal discharge, nasal secretions and droplets, ear secretions, perspiration, mucus, stool, and/or amniotic, spinal, wound, or abscess fluid. Analytes under test may include any analytes normally present in the biological sample and/or present in the biological sample abnormally, e.g. only as a result of the person providing the sample having one or more specific target or non-target conditions.

In one embodiment, the first target condition may be pregnancy, the first analyte may be human chorionic gonadotropin (hCG) and the second analyte may be luteinizing hormone (LH). hCG is a hormone produced during pregnancy and therefore measurement of the levels of hCG in a biological sample of blood or urine is a well known procedure for testing pregnancy in women. While the levels of hCG rapidly increase after conception, to detect pregnancy very soon after conception, which is highly desirable, test apparatus must be relatively sensitive to low levels of hCG.

Low levels of hCG are present, however, in urine and blood in the general population of women. This background level of hCG varies according to a woman's menstrual cycle and is elevated during the period of ovulation. It is also elevated around the peri-menopause and, to a lesser extent, in post-menopausal women. This creates a problem for pregnancy testing in that the level of hCG indicative of pregnancy in women varies depending on the background level of hCG (the 'physiological noise') that results from their stage in the menstrual cycle and/or their stage in life. While apparatus that is highly sensitive to hCG may be capable of indicating pregnancy very soon after conception, it is more susceptible to yielding false positive indications of pregnancy due to its sensitivity to background noise that can occur as a result of non-pregnant production of hCG known as pituitary hCG. This is clearly undesirable.

The present disclosure recognises, however, that higher levels of LH are present in blood or urine at times when hCG is at higher background levels. For example, an LH surge occurs approximately 24-48 hours before ovulation and LH remains elevated during ovulation. It has been found, for example, that in urine samples provided by women where the level of hCG is >1 IU/L, a level that can provide an early indication of pregnancy, a majority of the women providing the samples were in fact subject to an LH peak. Accordingly, at least until now, identification of pregnancy based on levels of hCG>1 IU/L has a very high potential to provide false positive indications. The relationship between LH and hCG may be due to cross-reactivity between the hCG assay and the LH assay, which are very similar proteins. However, technical information associated with instruments detecting these proteins has indicated that there may be no cross-reactivity. Indeed, there exists data which suggests that the hCG is made by the anterior pituitary, which is also where LH is synthesised.

Regardless of the reasons for the relationship or correlation between detected levels of hCG and LH in blood or urine, by detecting a relatively high level of LH in a biological sample, it can be determined that the person providing the sample is relatively more likely to provide a false positive indication of pregnancy due to higher background levels of hCG in the sample. Equally, by detecting a relatively low level of LH in a biological sample, it can be determined that the person providing the sample is relatively less likely to provide a false positive indication of pregnancy. Generally, this can allow 'filtering' of the physiological noise, facilitating sensitive and specific identification of pregnancy based on detection of hCG at lower levels than would otherwise be possible. The same filtering approach can be applied to other target conditions and/or using other analytes.

In one embodiment of the present disclosure the apparatus and method may be configured to identify a person as being pregnant if the level of hCG in the sample is above a threshold level, wherein the threshold level is varied dependent on the level of LH in the sample. In particular, the threshold level for hCG may be increased or decreased in accordance with a level of LH determined to be present in the sample. The increase may be linear, stepped, logarithmic or otherwise. The threshold level for hCG may be varied continuously or discretely based on the level of LH present. Where the hCG threshold level is varied discretely, the variation may be between e.g., two distinct threshold levels only, although more than two threshold levels, e.g. three, four or more threshold levels may also be used. While variation of threshold levels in relation to hCG and LH is now described, the same approach may be taken in relation to other analytes used to identify the same or other target conditions in accordance with the present disclosure.

As an example of discrete variation, a particular threshold level for LH ($T_{LH}$) may be used and, if the level of LH present is <$T_{LH}$, the threshold level for hCG ($T_{hCG}$) may be set at a relatively low level ($T_{hCG\_low}$) and, if the level of LH present is ≥$T_{LH}$, the threshold level for hCG may be set at a relatively high level ($T_{hCG\_high}$). In this example, if the LH level present is <$T_{LH}$ then pregnancy would be identified only if the hCG level was >$T_{hCG\_low}$. On the other hand, if the level of LH present was ≥$T_{LH}$ then pregnancy would be identified only if the hCG level was >$T_{hCG\_high}$. This example is represented in tabular form in Table 1a below. By taking the approach described, a highly accurate test may be provided, while allowing for some cross reactivity of hCG with LH.

The difference between $T_{hCG\_low}$ and $T_{hCG\_high}$ may be at least 5 IU/L, at least 10 IU/L or at least 15 IU/L or otherwise. In one embodiment, $T_{LH}$ may be about 20 IU/L, $T_{hCG\_low}$ may be about 1 IU/L and $T_{hCG\_high}$ may be about 20 IU/L, for example. It has also been determined that $T_{hCG\_low}$ levels of about 1.0 to 2.0 IU/L, or about 1.3 to 1.9 IU/L, or about 1.3 to 1.8 IU/L, or about 1.3 to 1.7 IU/L, or about 1.4 to 1.6 IU/L or about 1.5 IU/L may be suitable, for example.

The levels for $T_{LH}$ and $T_{hCG}$ may be changed, however, to achieve a desirable balance between producing a sensitive test and reducing the possibility of physiological noise affecting the accuracy of the test. Furthermore, the levels may be varied depending on changes in diagnostic practices in the medical industry and/or legal and regulatory requirements.

TABLE 1a

| LH level | hCG level | Pregnancy |
|---|---|---|
| <$T_{LH}$ | >$T_{hCG\_low}$ | Yes |
| <$T_{LH}$ | <$T_{hCG\_low}$ | No |
| ≥$T_{LH}$ | >$T_{hCG\_high}$ | Yes |
| ≥$T_{LH}$ | <$T_{hCG\_high}$ | No |

The example discussed above with reference to Table 1a uses two distinct hCG threshold levels ($T_{hCG\_low}$ and $T_{hCG\_high}$), which levels are selected for the identification of pregnancy based on the level of LH present in the sample. As also discussed, however, more than two distinct hCG threshold levels may be used in apparatus and methods according to the present disclosure.

Threshold levels for hCG may be selected for the identification of pregnancy based on the level of LH present in the sample falling in one of a corresponding number of LH ranges. For example, the apparatus and methods of the present disclosure may:

identify a level of the hCG in the biological sample;
identify a level of the LH in the biological sample;
determine which of a plurality of discrete LH ranges the identified level of LH falls within, a different hCG threshold level being associated with each one of the LH ranges;
select the hCG threshold level that is associated with the LH range in which the identified level of LH falls within; and
identify pregnancy in the body if the identified level of hCG is above the selected hCG threshold level.

There is generally no limit to the number of hCG threshold levels that may be used in apparatus and methods according to the present disclosure, each hCG threshold level being associated with a different LH range. In effect, the greater the number of threshold levels and ranges that are used, the closer the apparatus and methods may come to employing a substantially continuous (e.g., pseudo-continuous) variation of the hCG threshold level for identifying pregnancy based on the level of LH present in the sample.

Where in the example above only two distinct threshold levels are used for hCG ($T_{hCG\_low}$ and $T_{hCG\_high}$), these levels are selected, in effect, based on the level of LH present in the sample falling in one of a first LH range and a second LH range, the first and second LH ranges being defined by a first LH threshold ($T_{LH}$). The first LH range includes all LH values below the first LH threshold level (<$T_{LH}$) and the second LH range includes all LH values above the first LH threshold level (≥$T_{LH}$).

Where, for example, three distinct threshold levels for hCG are used, these levels may be selected based on the level of LH present in the sample falling in one of three LH ranges, i.e. a first LH range, a second LH range and a third LH range. The first, second and third LH ranges are defined by first and second LH threshold levels, the second LH threshold level being higher than the first LH threshold level. The first LH range includes all LH values below the first LH threshold level, the second LH range includes all LH values between the first LH threshold level and the second LH threshold level, and the third LH range including all values above the second LH threshold level. A first hCG threshold level is associated with the first LH range, a second hCG threshold level is associated with the second LH range; and a third hCG threshold level is associated with the third LH range.

The first, second and third LH ranges may be considered a low LH range, an intermediate LH range and a high LH range, respectively. The first LH threshold level may be considered a low LH threshold level ($T_{LH\_low}$) and the second LH threshold level may be considered a high LH threshold level ($T_{LH\_high}$). The first hCG threshold level may be considered a low hCG threshold level ($T_{hCG\_low}$), the second hCG threshold level may be considered an intermediate hCG threshold level ($T_{hCG\_mid}$) and the third hCG threshold level may be considered a high hCG threshold level ($T_{hCG\_high}$).

If the level of LH present is below the low LH threshold level ($<T_{LH\_low}$), i.e. it is in the low LH range, the hCG threshold level ($T_{hCG}$) is set at the low hCG threshold level ($T_{hCG\_low}$). If the level of LH present is between the low LH threshold level and the high LH threshold level ($\geq T_{LH\_low}$; $<T_{LH\_high}$), i.e. it is in the intermediate LH range, the threshold hCG level is set at the intermediate hCG threshold level ($T_{hCG\_mid}$). If the level of LH present is above the high threshold LH level ($\geq T_{LH\_high}$), i.e. it is in the high LH range, the threshold hCG level is set at the high threshold hCG level ($T_{hCG\_high}$). In this example, if the LH level present is in the low LH range ($<T_{LH\_low}$), then pregnancy would be identified only if the hCG level was above the low hCG threshold level ($>T_{hCG\_low}$). If the level of LH present was in the intermediate LH range ($\geq T_{LH\_low}$, $<T_{LH\_high}$), then pregnancy would be identified only if the hCG level was above the intermediate hCG threshold level ($>T_{hCG\_mid}$). If the level of LH present was in the high LH range ($\geq T_{LH\_high}$), then pregnancy would be identified only if the hCG level was above the high hCG threshold level ($>T_{hCG\_high}$). This example is represented in tabular form in Table 1b below. By taking the approach described, another highly accurate test may be provided, while allowing for some cross reactivity of hCG with LH.

Increasing the number of hCG threshold levels and associated LH ranges may reduce the possibility that pregnancy would be identified falsely. For example, when it is possible to identify the LH level as falling in an intermediate LH range (e.g., instead of falling at an upper end of a low LH range), an intermediate hCG threshold level can be used in place of a low hCG threshold level to reduce the likelihood of a false positive test occurring, while still achieving a relatively sensitive test.

The difference between $T_{hCG\_low}$ and $T_{hCG\_mid}$ may be at least 2 IU/L, at least 3 IU/L, at least 5 IU/L, at least 10 IU/L or at least 15 IU/L or otherwise. The difference between $T_{hCG\_mid}$ and $T_{hCG\_high}$ may be at least 2 IU/L, at least 3 IU/L, at least 5 IU/L, at least 10 IU/L or at least 15 IU/L or otherwise. The difference between $T_{LH\_low}$ and $T_{LH\_high}$ may be at least 5 IU/L, at least 10 IU/L, at least 15 IU/L, at least 20 IU/L or otherwise.

In one embodiment, $T_{LH\_low}$ may be about 15 IU/L, $T_{LH\_high}$ may be about 30 IU/L, $T_{hCG\_low}$ may be about 1.5 IU/L, $T_{hCG\_mid}$ may be about 5 IU/L or about 10 IU/L, and $T_{hCG\_high}$ may be about 20 IU/L.

The threshold levels for LH and hCG ($T_{LH}$ and $T_{LH\_high}$ may be changed, however, to achieve a desirable balance between producing a sensitive test and reducing the possibility of physiological noise affecting the accuracy of the test. Furthermore, the levels may be varied depending on changes in diagnostic practices in the medical industry and/or legal and regulatory requirements.

TABLE 1b

| LH level | hCG level | Pregnancy |
| --- | --- | --- |
| $<T_{LH\_low}$ | $>T_{hCG\_low}$ | Yes |
| $<T_{LH\_low}$ | $<T_{hCG\_low}$ | No |
| $\geq T_{LH\_low}$, $<T_{LH\_high}$ | $>T_{hCG\_mid}$ | Yes |
| $\geq T_{LH\_low}$, $<T_{LH\_high}$ | $<T_{hCG\_mid}$ | No |
| $\geq T_{LH\_high}$ | $>T_{hCG\_high}$ | Yes |
| $\geq T_{LH\_high}$ | $<T_{hCG\_high}$ | No |

Nonetheless, alternative approaches to identifying pregnancy may be taken in accordance with the present disclosure. For example, in one embodiment, the apparatus and method may be configured such that pregnancy is identified based on a determination that hCG is above a threshold hCG level in the sample and LH is below a threshold LH level in the sample, without any variation of either threshold level. In an alternative embodiment, the apparatus may be configured to determine that it is not possible to identify pregnancy, regardless of the level of hCG present in the sample, due to the level of LH being above a threshold LH level.

As indicated further above, the apparatus and method may be configured for identifying more than one target condition, e.g. first and second target conditions, which target conditions may capable of being present in the body at the same time, or which target conditions may be mutually exclusive. Accordingly, while in the example above identification of LH is effectively used to identify a non-target condition (ovulation period or menopause) for the sole purpose of the accurate identification of a target condition (pregnancy), in other embodiments, a second condition may also be treated as a target condition and therefore information about the second condition may be presented to the user. Identification of a second target condition may be based on identification of the second analyte only, or it again may be based on identification of both the first and second analytes.

Staying with a pregnancy example, the first analyte may be hCG and the first target condition may be pregnancy, and the second analyte may be LH and the second target condition may be the ovulation phase in a menstrual cycle.

As discussed, an LH surge occurs approximately 24-48 hours before ovulation and LH remains elevated during ovulation. Accordingly, while identification of LH can be used to determine if hCG levels are likely to be elevated in the person under test, it may also be used to identify if the person is in (or close to) the ovulation phase of their menstrual cycle, a phase around which sexual intercourse is most likely to result in pregnancy.

Following from this, in one embodiment of the present disclosure the apparatus and method may be configured, for example, to (i) identify a person as being pregnant if the level of hCG in the sample is above one or more threshold levels, wherein the hCG threshold level is varied dependent on the level of LH in the sample, and (ii) if the person is not identified as being pregnant, identify the person as being in the ovulation phase if the level of LH in the sample is above a threshold level. The arrangement may be similar to one or both of the preceding examples except, when the level of LH is above $T_{LH}$ or above $T_{LH\_high}$, and the level of hCG is below $T_{hCG\_high}$ or $T_{hCG\_mid}$, the person providing the sample may be identified not only as being not pregnant, but identified as being in the ovulation phase of their menstrual cycle. These examples, which are adaptations of the approaches represented in Tables 1a and 1b above, are represented in tabular form in Tables 2a and 2b respectively, set forth below.

TABLE 2a

| LH level | hCG level | Ovulation phase | Pregnancy |
|---|---|---|---|
| $<T_{LH}$ | $>T_{hCG\_low}$ | No | Yes |
| $<T_{LH}$ | $<T_{hCG\_low}$ | No | No |
| $\geq T_{LH}$ | $>T_{hCG\_high}$ | No | Yes |
| $\geq T_{LH}$ | $<T_{hCG\_high}$ | Yes | No |

TABLE 2b

| LH level | hCG level | Ovulation phase | Pregnancy |
|---|---|---|---|
| $<T_{LH\_low}$ | $>T_{hCG\_low}$ | No | Yes |
| $<T_{LH\_low}$ | $<T_{hCG\_low}$ | No | No |
| $\geq T_{LH\_low}; <T_{LH\_high}$ | $>T_{hCG\_mid}$ | No | Yes |
| $\geq T_{LH\_low}; <T_{LH\_high}$ | $<T_{hCG\_mid}$ | No | No |
| $\geq T_{LH\_high}$ | $>T_{hCG\_high}$ | No | Yes |
| $\geq T_{LH\_high}$ | $<T_{hCG\_high}$ | Yes | No |

Thus, the apparatus and method of the present disclosure may provide means for identifying both pregnancy and the ovulation phase. Since the apparatus may be a unitary device, e.g. a hand-held device, the device may therefore be used easily at home, when a woman is trying to conceive, or contrarily as a contraceptive device when they are trying not to conceive, and also when they are pregnant. The device may therefore provide a combined ovulation prediction kit (OPK) and home pregnancy test (HPT).

In embodiments of the present disclosure, the apparatus and method may utilise one or more lateral flow test strips, which may employ principles of immunochromatography, for example. The apparatus and method may be configured to identify each of the analytes using respective test strips. Alternatively, a single test strip may be used to identify more than one or all of the analytes. In the latter case, the apparatus may provide cost savings since a single test strip may be used to test for multiple conditions e.g. both ovulation and pregnancy, and the apparatus may be simpler to use than traditional home pregnancy and ovulation test kits.

Follicle Stimulating Hormone (FSH), estradiol and/or progesterone hormones, or their metabolites, may be monitored in place of the LH hormone in some embodiments and examples, e.g., in place of the LH hormone used in the examples set forth above, which hormones are also present in urine and blood of the general population of women at levels that vary during the menstrual cycle.

The apparatus and method may employ a reader to identify at least the first and second analytes. The reader may include a photodetector capable of monitoring light reflection or light output at one or more test portions located on the one or more test strips, for example. At least where multiple analytes are to be identified in a single test strip, the test strip may employ fluorescent structures, e.g. quantum dots, as labels for the respective analytes, which structures may be configured to fluoresce at different wavelengths such that the presence of the different structures can be monitored independently, e.g. by a multi-wavelength photodetector, or by separate photodetectors tuned to different wavelengths.

The reader may comprise a processor for processing signals from the one or more photodetectors and identifying the one or more target analytes from the signals. The processor may be connected to a display for presenting information about identification of target conditions to the user.

In an aspect of the present disclosure, there is provided a lateral flow test strip adapted to identify both a first analyte that provides an indicator of pregnancy and a second analyte that provides an indicator of the ovulation phase in a menstrual cycle.

In another aspect of the present disclosure, there is provided a lateral flow test strip adapted to identify both human chorionic gonadotropin (hCG) and luteinizing hormone (LH).

In an aspect of the present disclosure, there is provided a lateral flow test strip for identifying in a biological sample a first analyte that provides an indicator of pregnancy and a second analyte that provides an indicator of an ovulation phase in a menstrual cycle, the test strip comprising:

a label-holding portion including a plurality of first and second label-conjugated antibodies, the first label-conjugated antibodies each comprising a first fluorescent structure and configured to bind to molecules of the first analyte in the biological sample to form labelled first analyte complexes, and the second label-conjugated antibodies each comprising a second fluorescent structure and configured to bind to molecules of the second analyte in the biological sample to form labelled second analyte complexes; and a test portion configured to immobilize both the labelled first analyte complexes and the labelled second analyte complexes;

wherein, upon excitation by light, the first fluorescent structures are configured to fluoresce at a first wavelength and the second fluorescent structures are configured to fluoresce at a second wavelength different from the first wavelength.

In another aspect of the present disclosure, there is provided a reader for identifying in a biological sample a first analyte that provides an indicator of pregnancy and a second analyte that provides an indicator of the ovulation phase in a menstrual cycle, the reader comprising:

a housing adapted to at least partially receive a lateral flow test strip and position a test portion of the test strip adjacent one or more light sources and one or more photodetectors, and a processor connected to the one or more photodetectors, wherein upon illumination of the test portion of the test strip by the one or more light sources, the processor is configured to receive signals from the one or more photodetectors indicative of (i) an intensity of light of a first wavelength emitted from a plurality of first fluorescent structures at the test portion; and (ii) an intensity of light of a second wavelength emitted from a plurality of second fluorescent structures at the test portion, wherein the second wavelength is different from the first wavelength.

In the preceding two aspects, the first analyte may be human chorionic gonadotropin (hCG) and the second analyte may be luteinizing hormone (LH).

The reader may comprise a display. The display may be connected to the processor.

The test strip and the reader may be adapted to identify, based on the signals from the one or more photodectectors, if a woman providing the biological sample is pregnant or not pregnant, or if the woman is pregnant or ovulating or neither pregnant nor ovulating. To this extent the reader may adapted to identify pregnancy and/or ovulation in accordance with discussions made with respect to preceding aspects of the present disclosure, and the reader may display the results of identification to the user via the display.

In another embodiment of the present disclosure, the first target condition may be prior subjection to myocardial infarction ("heart attack"), the first analyte may be Troponin T and the second analyte may be an analyte providing a marker of renal failure such as creatinine A common marker analyte used for detecting if a person has suffered myocardial infarction (MI) is Troponin T (TNT). TNT is a protein found almost exclusively in heart muscle and is involved in the contraction of the muscle. If a person has been the subject of MI, their heart muscle is oxygen deprived and some of the cells in the heart cannot maintain electrochemical balance and therefore the myocytes can lyse. Myocyte lysis results in a rise in TNT in the blood providing evidence that a heart attack has occurred. TNT levels rise over hours to days and remain high for about 1 to 2 weeks after MI.

Normally, TNT is cleared by the kidneys. However, if a person has renal failure, it is possible to have a background level of TNT that has not been cleared. Renal failure may result in higher levels of TNT and thus lead to false positive indications in diagnostic assays that analyse TNT levels only. Serious complications might arise from such a mistake, e.g. through unnecessarily providing thrombolysis to a patient as a means of treating MI and exposing them to subsequent risks such as intracranial haemorrhage, for example.

An example marker analyte for renal failure is creatinine. Creatinine is filtered out of the blood by the kidneys and therefore, if renal function is inhibited, the level of creatinine in blood rises. A creatinine clearance (CrCL) test may be used to assess renal function.

Following from this, in one embodiment of the present disclosure the apparatus may be configured to identify a person as having suffered MI if the level of TNT identified in the sample is above a threshold level, wherein the threshold level is varied dependent on the level of creatinine identified in the sample.

Nonetheless, alternative approaches may be taken. For example, in one embodiment, the apparatus may be configured such that a person can be deemed as having suffered MI based on a determination that TNT is above a threshold TNT level in the sample and creatinine is below a threshold creatinine level in the sample. In an alternative embodiment, the apparatus may be configured to determine that it is not possible to identify that a person has suffered MI, regardless of the level of TNT present in the sample, due to the level of creatinine found in the sample.

In embodiments of the present disclosure, the second or any successive analyte identified may be an analyte that is normally present in the biological sample under test. The analyte may therefore be used as a form of sample control, identifying in particular whether enough of the sample is present to enable identification of the first target condition by virtue of identification of at least the first analyte. For example, the biological sample may be nasal mucus, the target condition may be influenza such as influenza A, the first analyte may be an influenza antigen such as an influenza viral nucleoprotein antigen and the second analyte may be mucin protein (MUC5A) which is normally present in nasal mucus.

Following from this, the apparatus and method may be configured such that:

a person can be identified as having influenza based on a determination that the influenza antigen is equal to or above a threshold antigen level ($T_{Flu}$) in the sample, regardless of the level of MUC5A protein in the sample;

a person can be identified as not having influenza based on a determination that the influenza antigen is below a threshold antigen level ($T_{Flu}$) in the sample and the level of MUC5A protein in the sample is equal to or above a threshold level ($T_{MUC5A}$); and/or the apparatus can indicate that identification of influenza in the person is not possible or unknown, due to the sample being inadequate in size, based on a determination that the influenza antigen is below a threshold antigen level ($T_{Flu}$) in the sample and the MUC5A protein is below a threshold MUC5A level in the sample ($T_{MUC5A}$).

When each of these approaches is combined, the apparatus and method may be configured to identify influenza in accordance with Table 3 below.

TABLE 3

| Influenza antigen level | MUC5A level | Influenza |
|---|---|---|
| $\geq T_{Flu}$ | Any | Yes |
| $< T_{Flu}$ | $\geq T_{MUC5A}$ | No |
| $< T_{Flu}$ | $< T_{MUC5A}$ | Unknown |

The apparatus and method may passively or actively identify target conditions. Passive identification of the first target condition, for example, may involve the apparatus displaying to the user separate information about the identification of the first and second analytes, whereupon the user can identify the first target condition, in accordance with the preceding discussions, based on their own interpretation of the separately displayed information about the first and second analytes. For example, the one or more test portions may display or not display a symbol, or display different symbols, dependent on the identification of the respective analytes. Active identification may involve the apparatus receiving data representative of the identification of the first and second analytes, processing this data to identify the target condition, and displaying information identifying the target condition(s) to the user. For example, the apparatus may display or not display a symbol, or display different symbols, dependent on the identification of the target condition.

The apparatus may comprise a processor, e.g. a computer processor, to process data relating to identification of the first analyte, the second analyte and/or the target condition. The processor may determine if measured levels of the first and/or second analytes are above, equal to, or below a threshold level and the processor may vary ("tune") threshold levels depending on the measured levels of the first and/or second analytes. The processor may be connected to a memory or other data storage device that stores information about one or more threshold levels, and may be connected to a display device, e.g. a digital display such an LCD or LED display, to display the information about the identification of at least the target conditions.

The one or more test portions may take a variety of different forms suitable for testing the respective analytes. For example, where the analytes hCG and LH are under test or otherwise, the one or more test portions may be comprised in one or more lateral flow means and may employ principals of immunochromatography (rapid flow tests) or otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of specific example with reference to the accompanying drawings, in which:

FIG. 10 shows a representation of a test device according to a fourth embodiment of the present disclosure;

FIGS. 11A and 11B show opposing side views of the device of FIG. 10, and FIG. 11C shows an end view of the device of FIG. 10.

FIG. 14C provides a table of percentages of false positive results predicted for samples in the experimental example, for different hCG threshold levels and with LH filtering based on different LH threshold levels;

DESCRIPTION OF EMBODIMENTS

Figure 1:
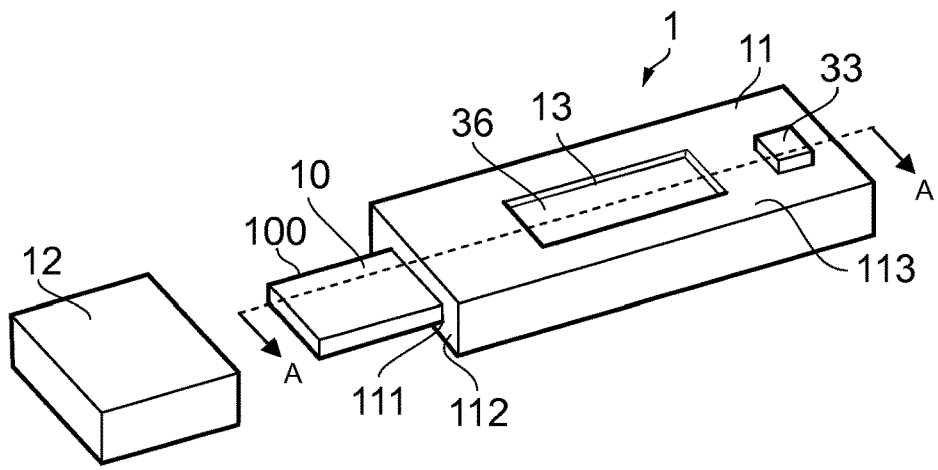
FIG. 1 shows an oblique view of a test device according to a first embodiment of the present disclosure.

Apparatus, in particular a test device 1, for identifying a target condition in a body according to a first embodiment of the present disclosure is shown in FIG. 1. The test device 1 is configured to test for pregnancy in a woman following receipt of a urine sample from the woman.

The test device 1 includes an elongate lateral flow test strip 10 and a casing 11. The test strip 10 is partially housed in the casing 11 with a sampling end 100 of the test strip 10 protruding from an opening 111 in an end surface 112 of the casing 11, allowing urine sample to be received directly thereon. The sampling end 100 of the test strip 10 is coverable by a cap 12. The test device 1 also includes an LCD display 36 visible through an opening 13 in a top surface 113 of the casing 11 for displaying results of testing.

The test device 1 is a hand-held device configured to identify pregnancy by identifying amounts (levels) of both hCG and LH hormone in the urine sample. As discussed above, hCG is an indicator (a marker) of pregnancy. However, the amount of hCG present in a woman's urine sample can be elevated outside of pregnancy, particularly during the ovulation phase of a woman's cycle, and around the menopause. At these times, LH is also elevated, and LH can therefore provide a marker for ovulation and menopause. However, particularly in relation to the current embodiment, LH can also provide a marker for identifying when hCG may be at higher background levels in the urine (or blood) of the person under test.

Figure 5A:
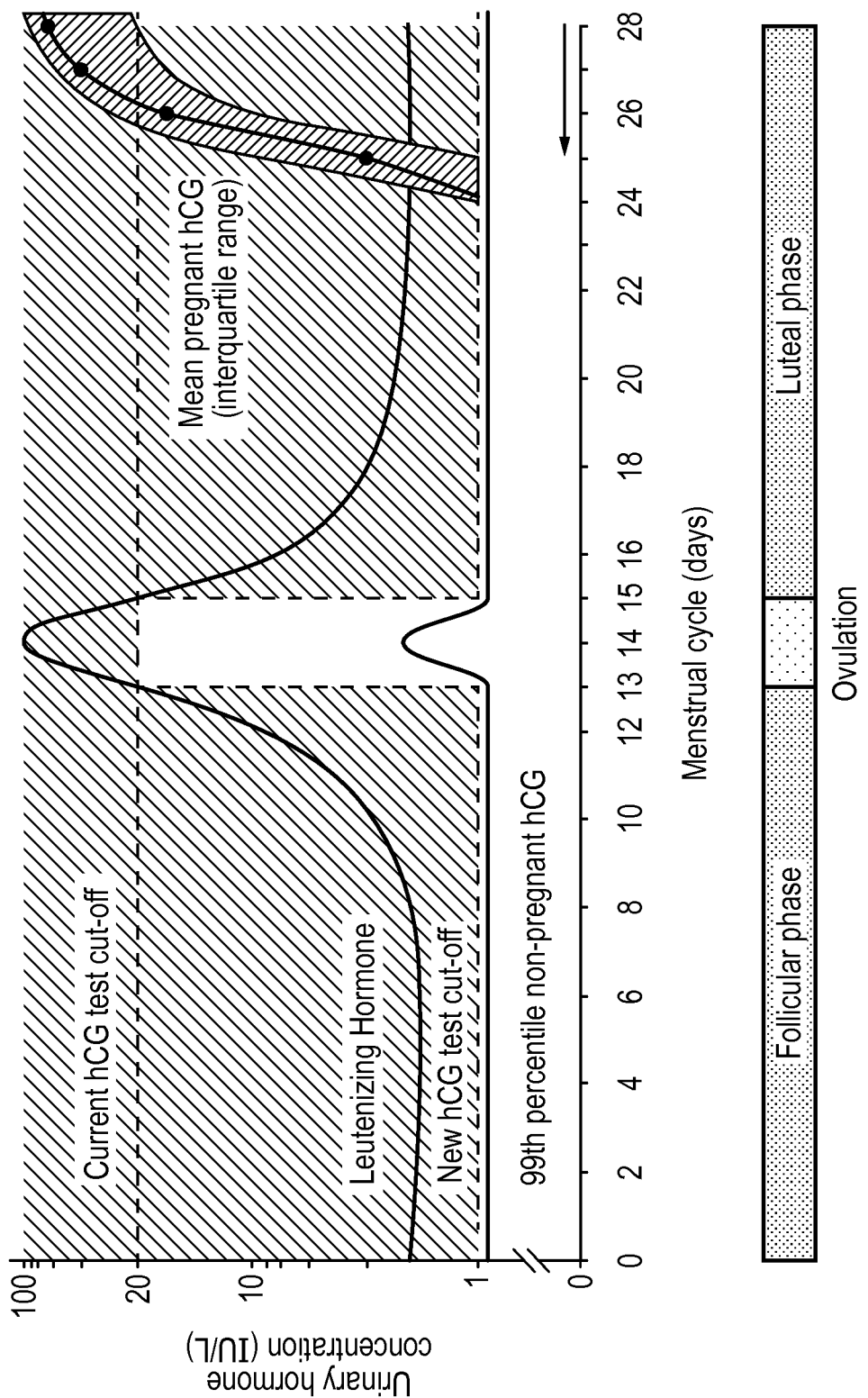
FIG. 5A shows a graph of example concentrations of hCG and LH in urine during the menstrual cycle.

Example changes in hCG and LH throughout the menstrual cycle, and during the first few days of pregnancy, are represent graphically in FIG. 5A. These changes, and changes during the menopausal period in an entire life cycle, are also represented graphically in FIG. 5B. As can be seen, the $99^{th}$ percentile level of hCG in urine of non-pregnant women (i.e. the normal background level of hCG) remains below 1 IU/L throughout the menstrual cycle except during the period around ovulation and menopause, where it increases above 1 IU/L. Accordingly, tests configured to identify pregnancy based simply on an hCG threshold level of 1 IU/L, for example, can provide false positive results during the ovulation phase of the menstrual cycle, and during menopause. For this reason, traditional pregnancy tests set an hCG threshold level of much greater than 1 IU/L, e.g. at about 20 IU/L, which is represented in FIG. 5A by the broken line described as "Current hCG test cut-off". As can be seen from the line at the right side of the graph, however, during the first two or three days of pregnancy the level of hCG in urine remains significantly below the current hCG test cut-off line. Accordingly, traditional pregnancy tests will commonly provide false negatives results during the first few days of pregnancy.

Figure 5B:
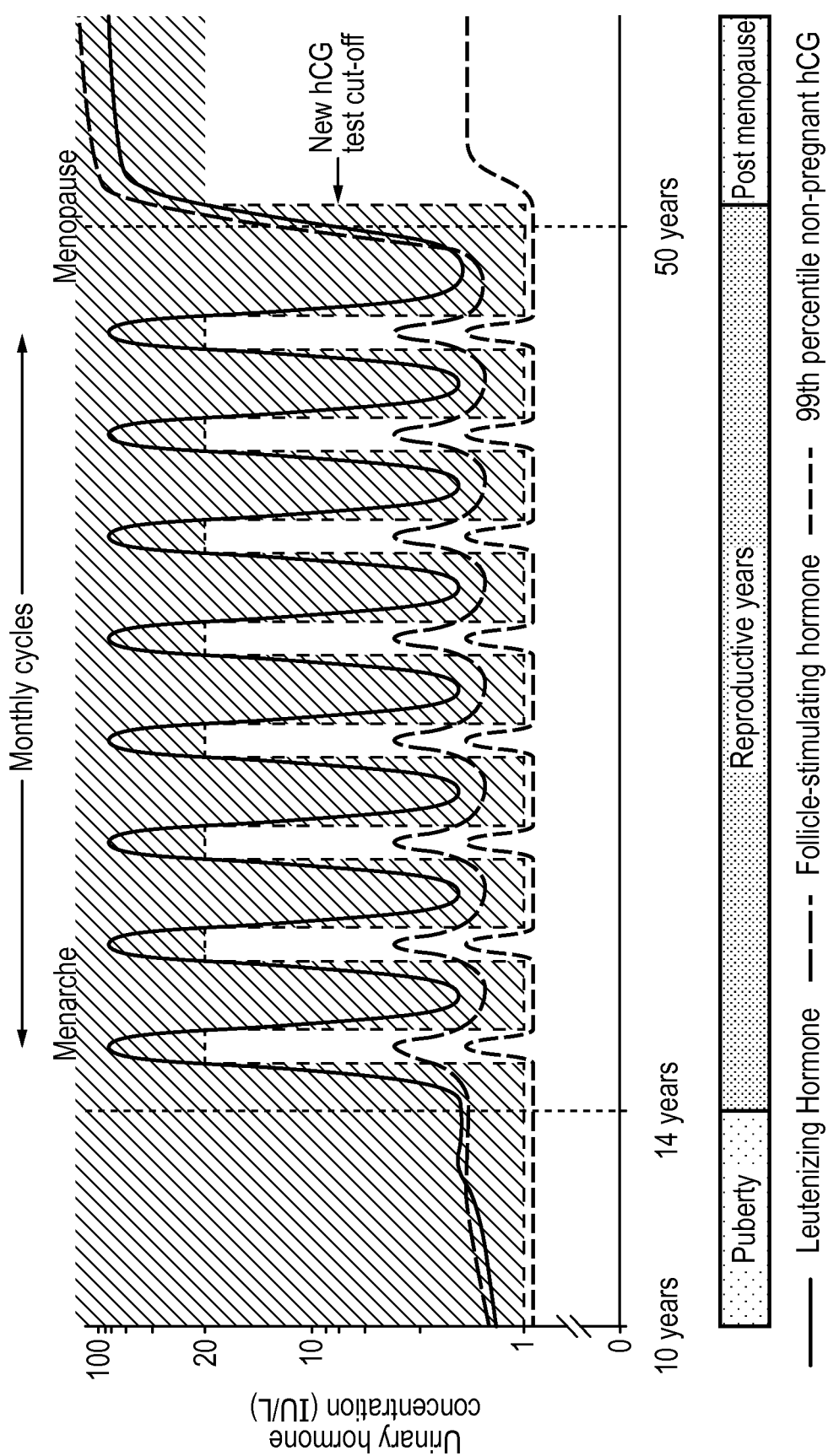
FIG. 5B shows a graph of example concentrations of hCG and LH in urine during a life cycle.

To allow earlier identification of pregnancy, the test device of the present embodiment is configured to set the hCG threshold level for identifying pregnancy at a higher level, e.g. at the current hCG test cut-off level, only when the person under test is at or near the ovulation phase of the menstrual cycle, or in menopause. The change in the hCG threshold level is represented in FIGS. 5A and 5B by the broken line described as "New hCG test cut-off". During the rest of the menstrual cycle and during menopause, the test device sets the hCG threshold level at a much lower level, 1 IU/L. To determine when the person under test is at or near the ovulation phase of their menstrual cycle or in menopause, the test device also identifies the levels of LH in the sample. As can be seen from the lines in the graphs representing changes in Leutenizing Hormone (LH) during the menstrual cycle and in menopause, LH surges in the period just before ovulation occurs, and remains elevated during ovulation and is elevated during menopause. In this embodiment, the LH threshold level at which the device sets the higher hCG threshold level is 20 IU/L.

Thus, the device 1 is configured to adjust the manner in which it identifies pregnancy based on identification of different levels of hCG and LH in the sample. The features of the device that enable this to be achieved in the present embodiment are discussed in more detail below.

Figure 2:
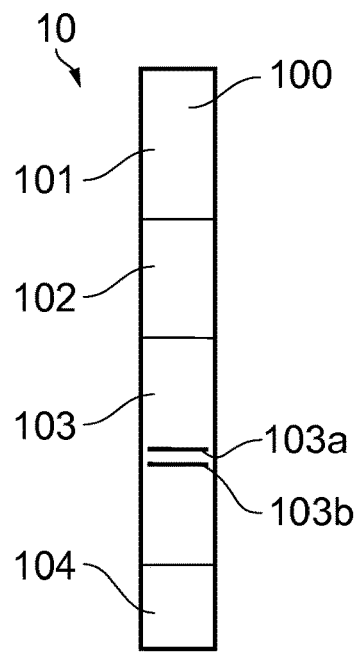
FIG. 2 shows a top view of a test strip used in the test device of FIG. 1.
Figure 3:
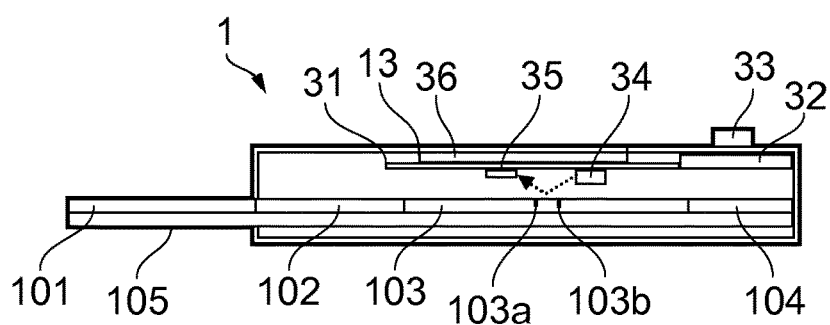
FIG. 3 shows a cross-sectional view of the test device of FIG. 1 along line A-A of FIG. 1.

Referring to FIGS. 2 and 3, the test strip 10 is a lateral flow test strip including different zones arranged sequentially along the length of the strip, including a sample receiving zone 101 at the sampling end 100, a label-holding zone 102, a test zone 103, and a sink 104. The zones 101-104 comprise chemically treated nitrocellulose, located on a waterproof substrate 105. The arrangement of the test zones 101-104 and substrate 105 is such that the urine sample, when directed onto the sample receiving zone 101, is absorbed into the sampling receiving zone 101 and travels under capillary action sequentially through the sample receiving zone 101, the label-holding zone 102, and the test zone 103 and accumulates finally at the sink 104.

The label-holding zone 102 comprises three types of label-conjugated antibodies in this embodiment. Two of the label-conjugated antibodies are designed to bind, respectively, with the hCG and LH hormone molecules to form complexes. The third label-conjugated antibody is designed for use as a control. The mix of the sample, the different LH and hCG complexes and the control label-conjugated antibody can travel to the test zone 103 and contact a test stripe 103a that contains immobilized compounds capable of binding the LH and hCG labelled complexes. When a sufficient amount of sample is present, the mix will continue through the text zone to contact a control stripe 103b capable of binding the control label-conjugated antibody.

In this embodiment, the three label-conjugated antibodies are labelled with different types of fluorescent quantum dots (QDs), configured to fluoresce at a different specific emission peak wavelengths following UV light excitation (e.g. 525, 625 and 800 nm, respectively). Accordingly, by illuminating the stripes 103a, 103b with UV light, the presence of the QD labels will result in a detectable light emission with different emission peaks. The intensity of the light emission (the size of the peaks) is indicative of the number of labelled complexes/antibodies bound to the stripes, which is in turn indicative of the prevalence of hCG and LH hormone in the sample and the amount of the sample that has reached the control stripe. As such, one or more wavelength sensitive photodetectors, forming part of a reader, can be used to identify the amounts of hCG and LH hormone in the sample through monitoring of the test stripe 103a. The one or more photodetectors can also be used to determine, through monitoring of the control stripe 103b, that a sufficient amount of sample has traveled through the test stripe 103a to the control stripe 103b and that binding of the labelled complexes has been successful.

Figure 4:
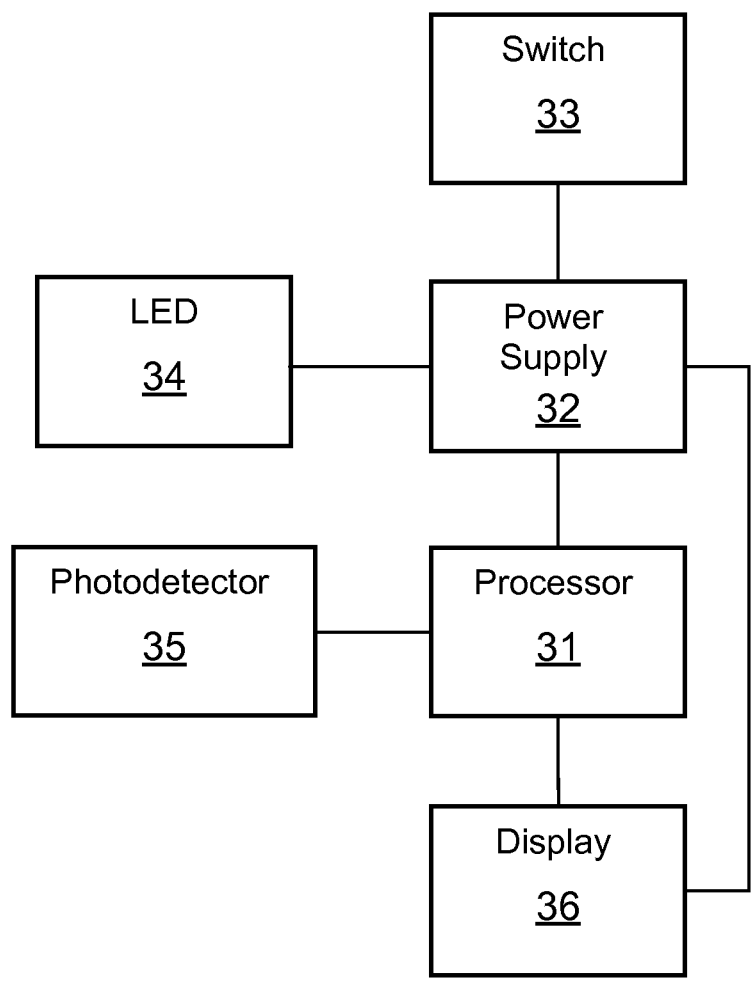
FIG. 4 shows a schematic representation of reading apparatus used in the test device of FIG. 1.

Referring to FIGS. 3 and 4, reading apparatus of the test device 1 is now described in more detail. The reading apparatus includes a printed circuit board having a processor 31, a power supply (battery) 32, a switch 33, a UV LED 34, a multi-wavelength photodetector 35 and the display 36. The LED 34 is configured to emit light in the UV spectrum (at about 300 to 400 nm), that is incident on the stripes 103a, 103b to cause excitation of the quantum dot labels located thereon. The multi-wavelength photodetector 35 in combination with the processor 31 is configured to detect the different intensities of light emitted from the quantum dots at each of the three distinct wavelengths.

In use, the cap 12 is removed from sampling end 100 of the test strip and a urine sample is directed onto the sample receiving zone 101. The cap 12 can be replaced and, after approximately 1 or 2 minutes, giving sufficient time for the lateral flow process to take place, the switch 33 can be depressed, causing flow of electricity from the power supply 32 to the LED 34, resulting in emission of UV light from the LED 34 that is incident on the stripes 103a, 103b of the test strip 10. The UV light results in excitation of any or all of the three types of quantum dots that may be immobilized as part of the respective labelled complexes at the stripes 103a, 103b, causing light emission at respective wavelength peaks. In combination with the multi-wavelength photodetector 35, the processor 31 is configured to determine the size of the emission peaks and identify from this (a) if the sample mix has arrived at the control stripe 103b and labelling has been effective, and if yes, identify (b) an amount of hCG present in the sample, and (c) an amount of LH present in the sample.

While a manual switch 33 is described above, in alternative embodiments, switching may be automated. For example, switching may be configured to occur upon replacement of the cap 12 onto the casing 11 or due to fluid activation, as the sample travels through a fluid-activated switch that may be provided in the device.

If it is identified there is insufficient amount of sample, the processor 31 is configured to cause the display 36 to present the words INVALID TEST.

If it is identified there is sufficient amount of sample, the processor 31 is configured to identify the levels of hCG and LH in the sample. Specifically, the processor in this embodiment is configured to determine if the level of LH is equal to or greater than an LH threshold level ($T_{LH}$) of 20 IU/L. If the level of LH present is less than the threshold level, the processor sets an hCG threshold level ($T_{hCG\_low}$) for identifying pregnancy of 1 IU/L, i.e. it identifies pregnancy only if the level of hCG is greater than 1 IU/L. On the other hand, if the level of LH is greater than or equal to the LH threshold level ($T_{LH}$) of 20 IU/L, the processor sets a higher hCG threshold level ($T_{hCG\_high}$) for identifying pregnancy of 20 IU/L, i.e. it identifies pregnancy only if the level of hCG is greater than 20 IU/L. The approach is represented in the graph of FIGS. 5A and 5B discussed above, and is also represented in Table 4a below.

TABLE 4a

| LH level | hCG level | Pregnancy | Display |
| --- | --- | --- | --- |
| <20 | >1 | Yes | PREGNANT |
| <20 | <1 | No | NOT PREGNANT |
| ≥20 | >20 | Yes | PREGNANT |
| ≥20 | <20 | No | NOT PREGNANT |

The LED may be carefully calibrated to ensure that the light emission from the LED is consistent from one device to the next, ensuring that a degree of excitation of the quantum dots is consistent. Additionally or alternatively, a calibration mechanism may be integrated into the device. A known quantity of quantum dots, configured to fluoresce at yet another wavelength, may be immobilized on the strip, e.g. at the test stripe. Depending on the intensity of the fluorescence detected from the known quantity of quantum dots, the processor may adjust its interpretation of the light emission from quantum dots that label the LH and hCG analytes. Additionally or alternatively, multiple LEDs may be used to excite the quantum dots with a view to suppressing the overall effect of any rogue LEDs.

If the processor 31 determines that the level of hCG is at or above the relevant hCG threshold level, the processor 31 causes the display 36 to present the words PREGNANT. If the processor 31 determines that the level of hCG is below the relevant hCG threshold level, the processor 31 causes the display 36 to present the words NOT PREGNANT.

In a second embodiment of a device according to the present disclosure, substantially the same device as described above with respect to the first embodiment is provided, but the device is configured to identify both pregnancy and ovulation phase in a woman's cycle. The difference between the devices of these two embodiments resides in the manner in which the processor 31 is configured to process information about the levels of LH and hCG in the sample and display information via the display 36.

As discussed, an LH surge occurs before ovulation and LH remains elevated during ovulation, and hCG levels are elevated during this period. Accordingly, in the first embodiment, identification of LH is used to determine if hCG levels are likely to be elevated in the person under test. However, in the second embodiment, identification of LH is used also to identify if the person is in (or close to) the ovulation phase of their menstrual cycle, a phase around which sexual intercourse is most likely to result in pregnancy.

Figure 6:
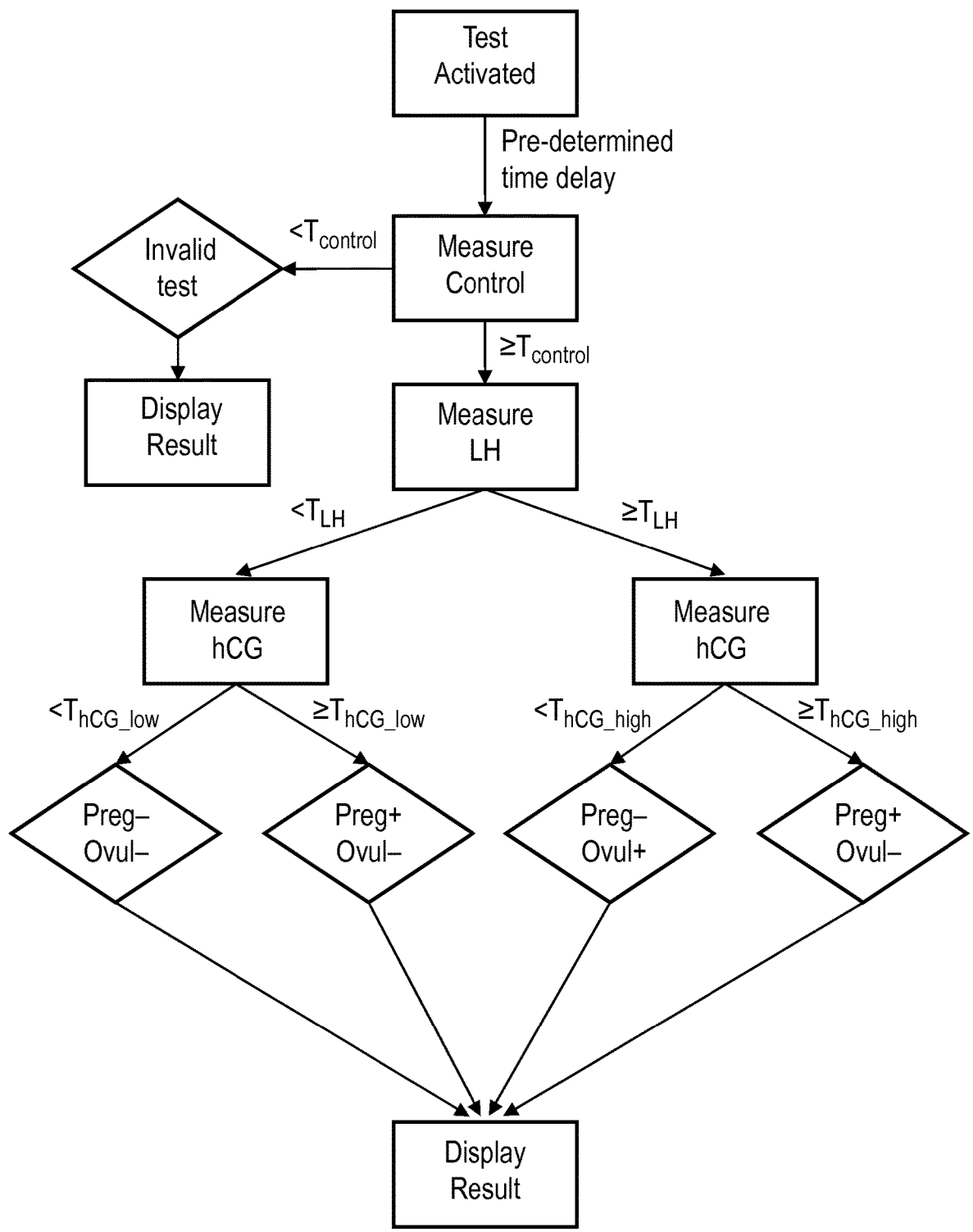
FIG. 6 shows a flow chart indicating processing steps of a test device according to a second embodiment of the present disclosure.

In this embodiment, if the level of LH is greater than or equal to the LH threshold level ($T_{LH}$), again the processor sets the higher hCG threshold level ($T_{hCG\_high}$) for identifying pregnancy. However, if the level of hCG is lower than $T_{hCG\_high}$, the processor identifies the ovulation phase of the woman's cycle and this information is conveyed to the user via the display 36. The same threshold level values for LH and hCG are used as those used in the preceding embodiment, although alternative values may be used. The approach is represented in Table 5a below. A flow-chart representing various processing steps taken by the processor in this second embodiment is also shown in FIG. 6.

TABLE 5a

| LH level | hCG level | Ovulation phase | Pregnancy | Display |
|---|---|---|---|---|
| <20 | >1 | No | Yes | PREGNANT |
| <20 | <1 | No | No | NOT PREGNANT NOT OVULATING |
| ≥20 | >20 | No | Yes | PREGNANT |
| ≥20 | <20 | Yes | No | OVULATING |

Thus, the device in this embodiment is configured to identify both pregnancy and ovulation. Since the device is a hand-held device, the device may be used at home, both while a woman is trying conceive (or contrarily as a contraceptive device), and also when they are pregnant. The device provides a combined ovulation prediction kit (OPK) and home pregnancy test (HPT).

The device is configured to allow removal of a used test strip from the casing 10, via the opening 111, and allow placement of a new test strip into the casing 10, via the same opening 111. Each time the strip is replaced, an identically configured test strip can be used, regardless of whether a woman is seeking to test for one or both of ovulation or pregnancy. In alternative embodiments, the device may be entirely a single-use device.

In the first embodiment of the present disclosure discussed above, two distinct threshold levels for hCG are used (1 IU/L and 20 IU/L), which are selected for the identification of pregnancy based on the level of LH present in the sample being in one of two respective ranges defined either side of a single LH threshold level (20 IU/L). While the values for the threshold levels for hCG and LH can be varied, adaptations of this embodiment can also employ more than two threshold levels for hCG and more than one threshold level for LH.

For example, in one adaptation of the first embodiment, the device is configured so that three distinct threshold levels for hCG are used, a low hCG threshold level ($T_{hCG\_low}$) of e.g., 1.5 IU/L, an intermediate hCG threshold level ($T_{hCG\_mid}$) of e.g., 5 IU/L and a high hCG threshold level ($T_{hCG\_high}$) of e.g., 20 IU/L. The different hCG threshold levels are used by the processor to identify pregnancy based on the level of LH present in the sample being in one of a low, intermediate and high LH range defined by a low LH threshold level ($T_{LH\_low}$) of e.g., 15 IU/L and a high LH threshold level ($T_{LH\_high}$) of e.g., 30 IU/L.

Specifically, the processor is configured to determine that the level of LH present is either: (i) in the low LH range if it is less than the low LH threshold level ($T_{LH\_low}$) of e.g., 15 IU/L, (ii) in the intermediate LH range if it is between the low and high threshold LH levels ($T_{LH\_low}$, $T_{LH\_high}$) of e.g., 15 IU/L and 30 IU/L; or (iii) it is in the high LH range if it is above the high threshold LH level ($T_{LH\_high}$) of e.g., 30 IU/L. If the level of LH present is in the low LH range, the processor sets the low hCG threshold level ($T_{hCG\_low}$) of e.g., 1.5 IU/L for identifying pregnancy, i.e. it identifies pregnancy only if the level of hCG is greater than 1.5 IU/L. If the level of LH present is in the intermediate LH range, the processor sets the intermediate hCG threshold level ($T_{hCG\_mid}$) of e.g., 5 IU/L for identifying pregnancy, i.e. it identifies pregnancy only if the level of hCG is greater than 5 IU/L. If the level of LH present is in the high LH range, the processor sets the high hCG threshold level ($T_{hCG\_high}$) of e.g., 20 IU/L for identifying pregnancy, i.e. it identifies pregnancy only if the level of hCG is greater than 20 IU/L. The approach is represented in Table 4b below.

TABLE 4b

| LH level | hCG level | Pregnancy | Display |
|---|---|---|---|
| <15 | >1.5 | Yes | PREGNANT |
| <15 | <1.5 | No | NOT PREGNANT |
| ≥15, <30 | >5 | Yes | PREGNANT |
| ≥15, <30 | <5 | No | NOT PREGNANT |
| ≥30 | >20 | Yes | PREGNANT |
| ≥30 | <20 | No | NOT PREGNANT |

A similar adaptation can be applied to the second embodiment of the present disclosure discussed above, in which embodiment the test device is adapted to identify both pregnancy and ovulation phase in a woman's cycle. For example, the test device of the second embodiment can be adapted so that it uses three distinct threshold levels for hCG, a low hCG threshold ($T_{hCG\_low}$) of e.g., 1.5 IU/L, an intermediate hCG threshold ($T_{hCG\_mid}$) of e.g., 5 IU/L and a high hCG threshold ($T_{hCG\_high}$) of e.g., 20 IU/L along with two LH threshold levels, a low LH threshold level ($T_{LH\_low}$) of e.g., 15 IU/L and a high LH threshold level ($T_{LH\_high}$) of e.g., 30 IU/L. In this configuration, if the level of LH is greater than the high LH threshold level ($T_{LH\_high}$), the processor sets the higher hCG threshold level ($T_{hCG\_high}$) for identifying pregnancy. However, if the level of hCG present is lower than the higher hCG threshold level ($T_{hCG\_high}$), the processor identifies the ovulation phase of the woman's cycle and this information is conveyed to the user via the display 36. The approach is represented in Table 5b below.

TABLE 5b

| LH level | hCG level | Ovulation phase | Pregnancy | Display |
|---|---|---|---|---|
| <15 | >1.5 | No | Yes | PREGNANT |
| <15 | <1.5 | No | No | NOT PREGNANT NOT OVULATING |
| ≥15, <30 | <5 | No | Yes | PREGNANT |
| ≥15, <30 | >5 | No | No | NOT PREGNANT NOT OVULATING |
| ≥30 | >20 | No | Yes | PREGNANT |
| ≥30 | <20 | Yes | No | OVULATING |

Figure 7:
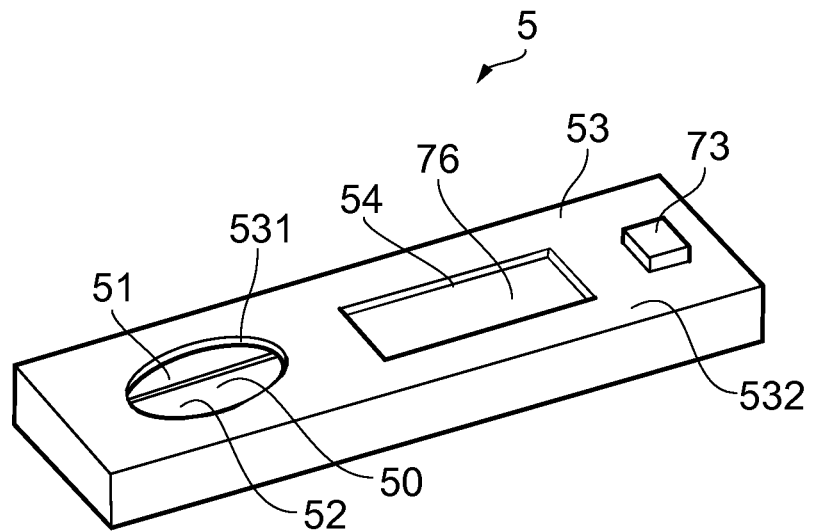
FIG. 7 shows an oblique view of a test device according to a third embodiment of the present disclosure.
Figure 8:
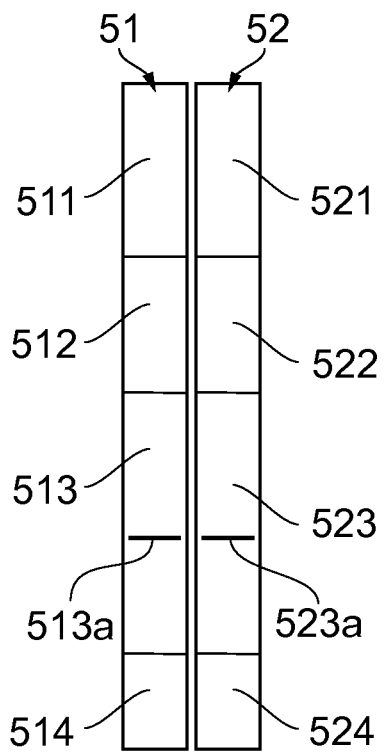
FIG. 8 shows a top view of test strips used in the test device of FIG. 7.

A test device 5, for identifying a target condition in a body according to a third embodiment of the present disclosure is represented in FIG. 7. The test device 5 is configured to test for prior subjection to myocardial infarction (MI or "heart attack").

The test device 5 includes two elongate lateral flow test strip 51, 52 and a casing 53. The test strips 51, 52 are each substantially housed in the casing 53 with a sampling end 50 of each of the test strips 51, 52 exposed through an opening 531 in a top surface 532 of the casing 53 allowing a blood sample, e.g. produced by a finger prick or applied via a pipette or otherwise, to be received directly thereon. Buffer solution can be added to increase the fluidity of the blood sample and assist lateral flow through the test strips 51, 52. The test device 5 also includes an LCD display 76 visible through an opening 54 in the top surface 532 of the casing 53 for displaying results of testing.

The test device 5 is a single-use hand-held device configured to identify prior subjection to myocardial infarction (MI) in a patient by identifying the amounts of both Troponin T (TNT) and creatinine in a blood sample from the patient. Levels of Troponin T in a urine sample provide an indication of whether or not a patient has suffered MI. However, the amount of Troponin T in the sample can be affected by the patient's ability to clear TNT from their system, meaning that background level of TNT may be higher in those who have renal dysfunction. The amount of creatinine in a urine sample is indicative of renal function. Following from this, the device 5 is configured to adjust the manner in which it identifies prior subjection to MI based on identification of different levels of TNT and creatinine in the sample. The manner in which this is achieved is discussed in more detail below.

Each of the test strips 51, 52 is a lateral flow test strip including zones arranged sequentially along its length, including a sample receiving zone 511, 521 at the sampling end 50, a label-holding zone 512, 522, a test zone 513, 523, and a sink 514, 524. Each of the test strips 51, 52 is therefore configured in a similar manner, and each works under similar principles, to the test strip 10 described above with respect to FIGS. 1 to 5b. However, in this embodiment, a single target analyte only is identified by each test strip respectively, and thus two strips are used (a TNT strip 51 and a creatinine strip 52). Furthermore, the test strips 51, 52 employ dye molecules as labels, rather than quantum dots, and they include no control stripes (although control strips may be used in alternative arrangements).

In more detail, at the label-holding zone 512 of the TNT test strip 51, label-conjugated antibodies are provided that bind with TNT antigens in the sample to form complexes. The mix of the sample and the labelled TNT complexes can travel to the test zone 513 and contact a test stripe 513a that contains immobilized compounds capable of binding the labelled TNT complexes.

Similarly, at the label-holding zone 522 of the creatinine test strip 52, label-conjugated antibodies are provided that bind with creatinine antigens in the sample to form complexes. The mix of the sample and the labelled creatinine complexes can travel to the test zone 523 and contact a test stripe 523a that contains immobilized compounds capable of binding the labelled creatinine complexes.

Figure 9:
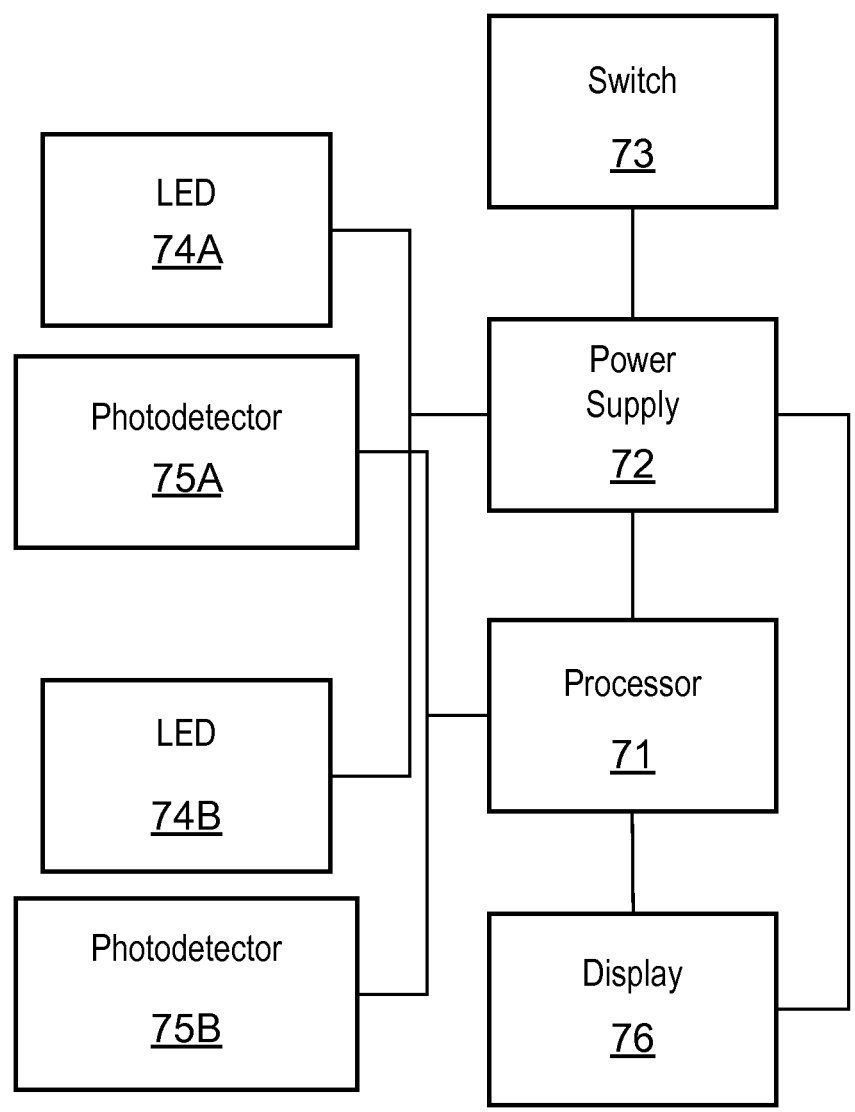
FIG. 9 shows a schematic representation of reading apparatus used in the test device of FIG. 7

Referring to FIG. 9, reading apparatus of the test device 5 is now described in more detail. The reading apparatus includes a printed circuit board having a processor 71, a power supply (battery) 72, a switch 73, first and second LEDs 74a, 74b, and first and second photodetectors 75a, 75b and the display 76. The first LED 74a is configured to emit light that is incident on the test stripe 513a of the TNT test strip 51 and the first photodetector 75a is configured to monitor the amount of light reflected from the test stripe 513a. Similarly, the second LED 74b is configured to emit light that is incident on the test stripe 513b of the creatinine test strip 52 and the second photodetector 75b is configured to monitor the amount of light reflected from the test stripe 523a. The amount of light reflected off the stripes is dependent on the number of dye molecules bound at the stripes and is therefore indicative of the amount of labelled TNT and creatinine complexes bound at the test stripes 513a, 523a of the TNT and creatinine test strips 51, 52, respectively. A partitioning wall is provided between each LED/photodetector combination to avoid light interference.

In combination with both photodetectors 75a, 75b, the processor 71 is configured to identify if the amount of TNT in the sample is greater than a starting TNT threshold of about 40 ng/L. However, the processor 71 is configured to increase this TNT threshold to about 100 ng/L if it determines that elevated levels of creatinine are present in the sample, particularly if the levels of creatinine are greater than 150-200 mmol/L for example.

If the processor 71 determines that the level of TNT is above the TNT threshold, the processor 71 causes the display 76 to present the words MI POSITIVE. If the processor 71 determines that the level of TNT is below the TNT threshold, the processor 71 causes the display 76 to present the words MI NEGATIVE.

Figure 12:
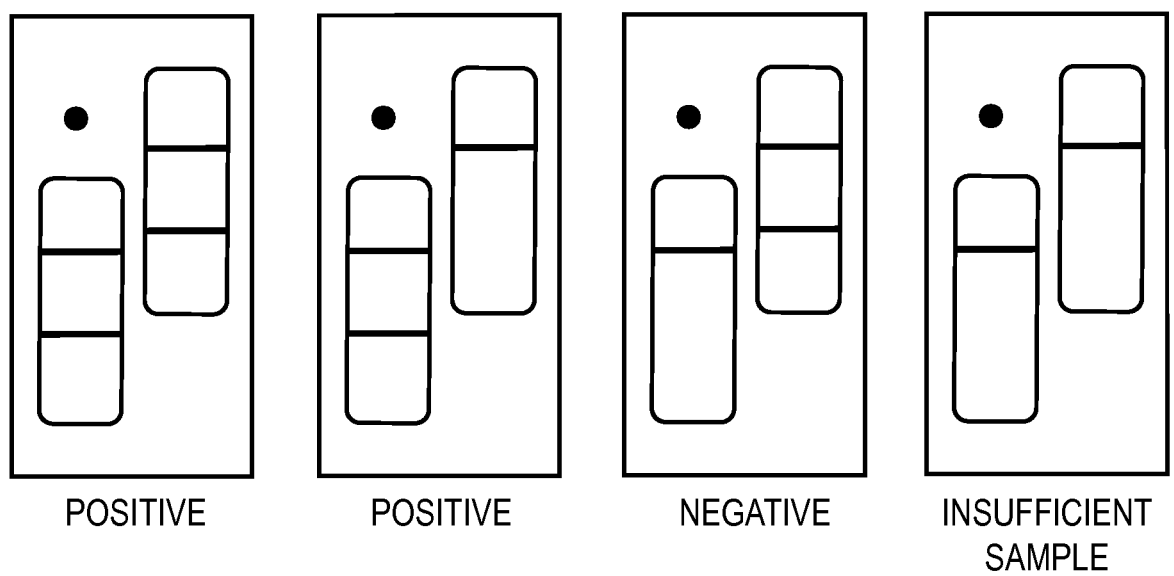
FIG. 12 shows representations of different arrangements of darkened stripes that give rise to various identification states of the device of FIG. 10.
Figure 13A:
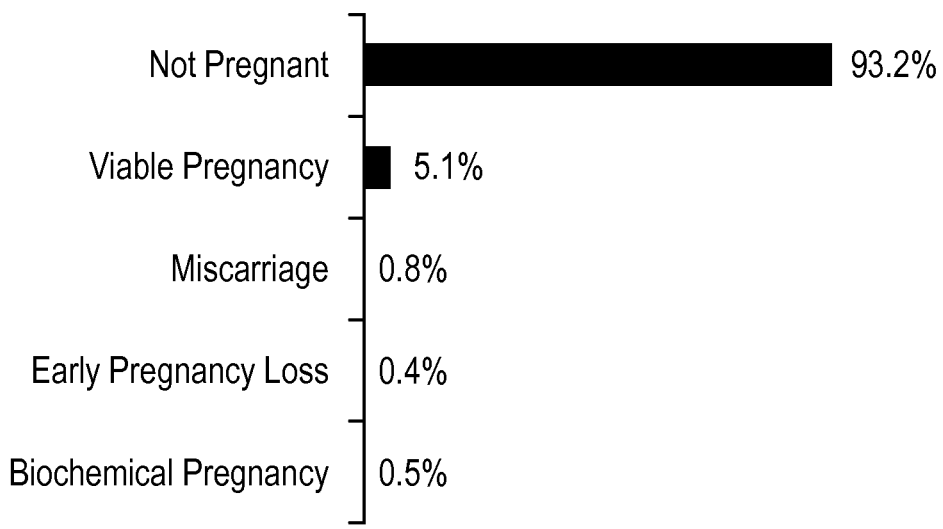
FIG. 13A shows distribution of urine samples by type, the samples being obtained from a plurality of women over multiple menstrual cycles, in relation to an experimental example of the present disclosure.
Figure 13B:
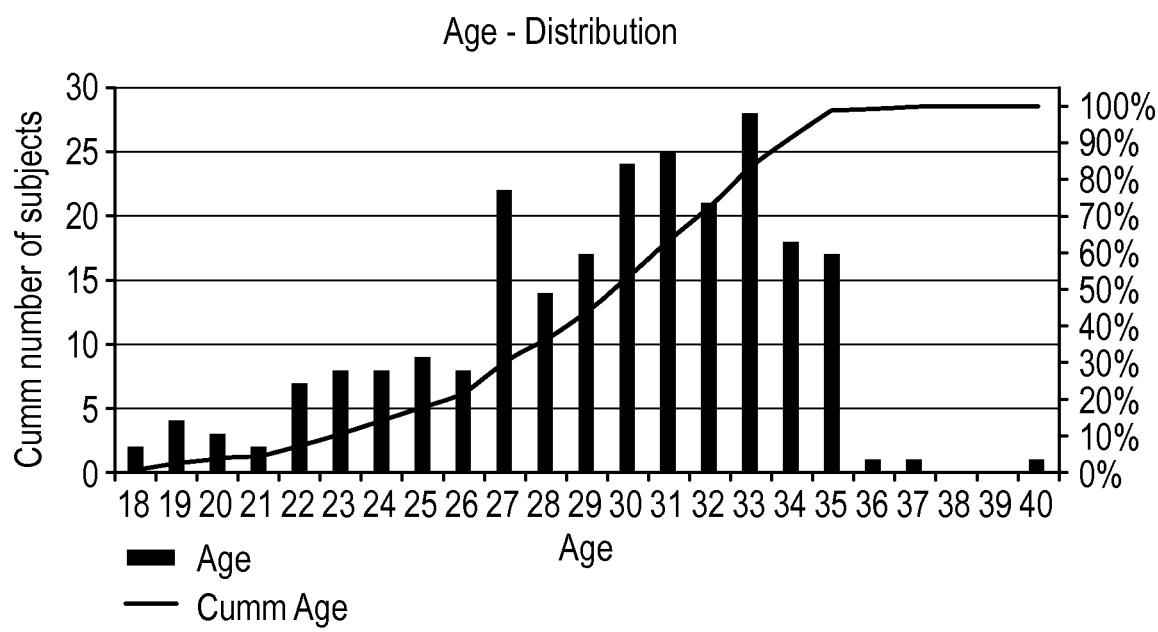
FIG. 13B represents the age distribution of the women providing the samples in the experimental example.

With reference to FIGS. 10 to 12, a device 8 according to a fourth embodiment of the present disclosure is now described. The device 8 may be considered to take, generally, a butterfly shape, due to the inclusion in the device of two wings 81, 82, either side of a housing 83, that are sufficiently pliable to flex around a person's nose 83, permitting the person to deposit a nasal mucus sample in a region between the two wings 81, 82, using a nose blowing technique. Once deposited, a buffer solution can be released from a reservoir in the housing 83 using a slide mechanism 84, increasing the fluidity of the sample and causing the sample to flow under capillary action through the device 8 to two lateral flow test strips 851, 852 located in the housing 83. Respective test portions of the lateral flow test strips 851, 852 are visible through windows 831, 832 in the housing 83. A test stripe 851a, 852a and a control stripe 851b, 852b are located at each of the test portions, as also illustrated in FIG. 12.

Overall, the configuration and function of the device 8 is substantially identical to the device described at page 22, line 28 to page 28, line 3, and depicted in FIGS. 7 to 14, of Applicant's PCT Publication No. WO2011/091473A1, the content of which is incorporated herein by reference. However, the presently disclosed device provides two test strips 851, 852 that are configured to identify in combination a single first target condition, influenza A. The first test trip 851 is configured to identify an influenza viral nucleoprotein antigen, which provides a marker of influenza A, and the second test strip 852 is configured to identify a mucin protein (MUC5A), which provides a marker of the size of the nasal mucus sample received by the device.

MUC5A is normally present in nasal mucus. Since buffer solution is used to assist in lateral flow of the sample through the test strips 851, 852, the sample, including MUC5A, can be diluted. If there is too much dilution, there is a risk that insufficient biological sample may reach test stripes 851a, 852a. Accordingly, the size of the sample reaching the test stripe 852a of one of the test strips 852, which has virtually identical lateral flow properties to the other of the test strips 851, can be assessed through identification of dye-labelled MUC5A complexes bound at the test stripe 852a.

The device 8 is configured to allow passive identification of influenza A through visual analysis by the user of test and control stripes 851a, 852a, 851b, 852b of each strip 851, 852. Particularly, identification is achieved through visually checking which of the stripes 851a, 852a, 851b, 852b are darkened shortly after application of nasal mucus and release of the buffer solution. When the test stripes 851a, 852a in particular are darkened, it is an indication that the amount of influenza A and MUC5A dye-labelled molecules immobilized at these test stripes, respectively, exceeds respective predetermined threshold levels.

The device 8 allows a person to be identified as having influenza A based on identification that the amount of the influenza A antigen is equal to or greater than the threshold antigen level (test stripe 851a is darkened), regardless of the level of MUC5A in the sample (test stripe 852a may or may not be darkened). The device also allows a person to be identified as not having influenza A based on a determination that the influenza A antigen is below a threshold antigen level (test stripe 851a is not darkened), when the level of MUC5A in the sample is equal to or above a threshold level (test stripe 852a is darkened). Further, the device informs a person that identification of influenza A in the person is not possible, due to the sample being inadequate in size, based on a determination that the influenza A antigen is below a threshold antigen level (test stripe 851a is not darkened), but the level of MUC5A in the sample is below a threshold level (test strip 851b is not darkened). The different arrangements of darkened stripes that give rise to the various identification states described above are represented to the user in pictorial form, as shown in FIG. 12, either on the device itself and/or in an accompanying instruction booklet.

While the device 8 of the fourth embodiment provides for passive identification of a target condition, in alternative embodiments, a reader may be included in the device 8 that analyses the test stripes 851a, 852a, 851b, 852b using one or more photodetectors and actively identifies the different identification states and presents information about the identification to the user via a digital display for example.

Experimental Example

Urine samples were obtained daily from 240 women. The age range of the women was 18 to 40 years and the average age of the women was 29.5 years. The samples were obtained across a cumulative total of 943 different menstrual cycles. Levels of hCG and LH in a total of 11,557 of the samples were measured using the Siemens Immulite 1000 and 2000 platforms. Each sample was ultimately categorised by sample type, based on whether or not the woman providing the sample was subsequently determined to have been pregnant or not pregnant at the time that she had provided the sample. Pregnancy was broken down into different categories including biochemical pregnancy, or pregnancy culminating in early pregnancy loss, miscarriage, or a viable pregnancy. A chart representing the distribution of the samples by type is provided in FIG. 13A and a chart representing the age distribution of the women is provide in FIG. 13B.

Multiple predictions of pregnancy or non-pregnancy were made for each sample by comparing (a) the measured hCG and LH levels of the sample with different combinations of hCG and LH threshold levels, and by comparing (b) the measured hCG level of the sample with different hCG threshold levels only. Approach (a) can be considered to apply LH 'filtering', whereas approach (b) can be considered to apply no such filtering. In (a), for each different combination of hCG and LH threshold levels, a positive result (i.e. pregnancy) was predicted only where the measured level of hCG was above the hCG threshold level and where the measured level of LH was below the LH threshold level. In (b), for each hCG threshold level, a positive result was predicted only where the measured level of hCG was above the hCG threshold level, without regard to the measured LH level. A negative result (i.e. non-pregnancy) was predicted in all other instances. Each predicted result was then compared with the sample type, to determine if the predicted result was a false positive result or a false negative result.

Figure 14A:
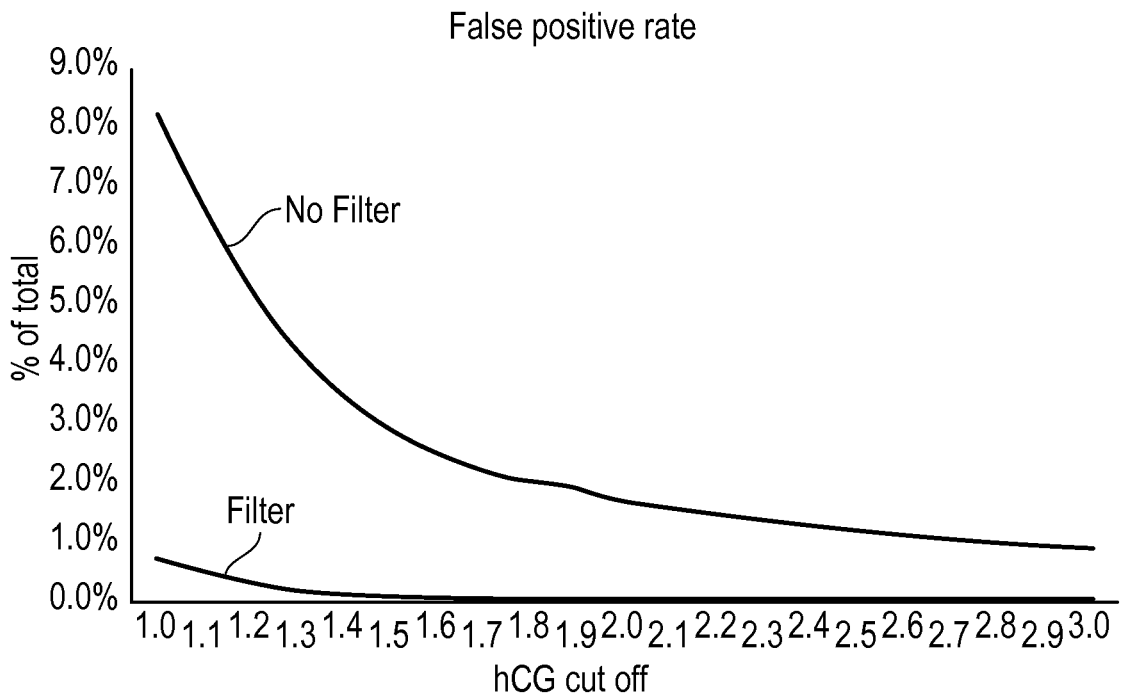
FIGS. 14A and 14B provide graphs showing percentages of false positive and false negative results, respectively, predicted for samples in the experimental example, for different hCG threshold levels and with and without the application of LH filtering based on an LH threshold level of about 20 IU/L.
Figure 14B:
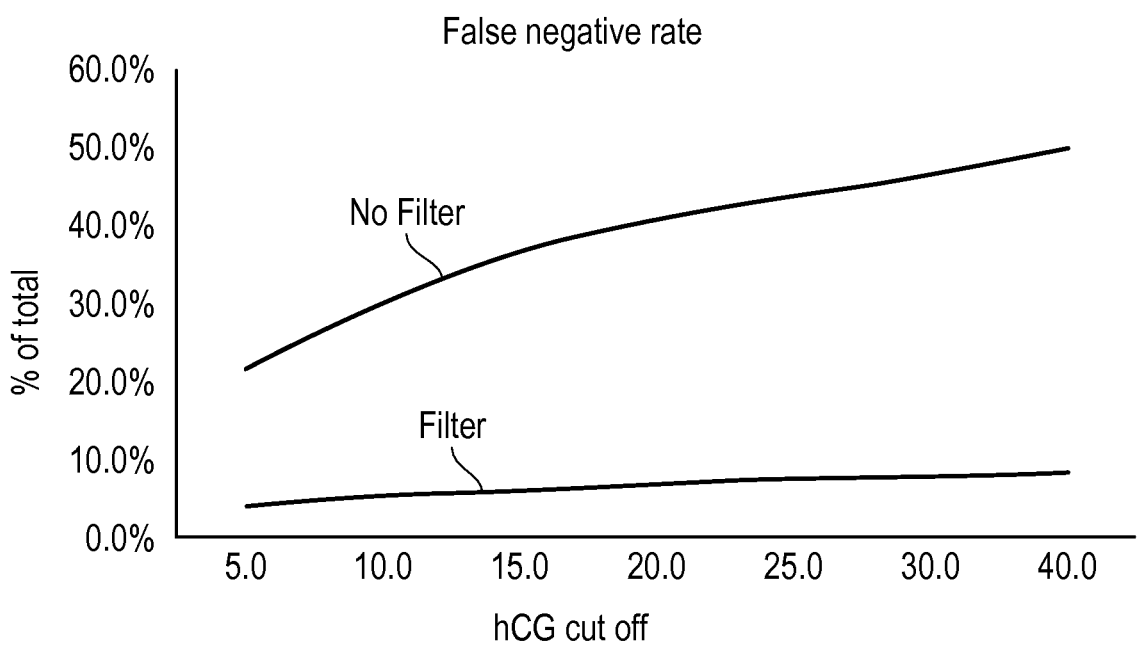

FIGS. 14A and 14B provide graphs showing the percentage of false positive and false negative results, respectively, which were predicted for different hCG threshold levels, (a) when LH filtering was applied, in particular an LH threshold level of about 20 IU/L in this instance and (b) when no LH filtering was applied.

FIG. 14C provides a table of percentages of false positive results that were predicted for hCG thresholds ranging from 1.0 IU/L to 3.0 IU/L when LH filtering was applied at LH thresholds ranging from 5 IU/L to 40 IU/L. The shaded area in the table, below the broken line, highlights all percentages of false positive results that were less than 0.1%.

Figure 15:
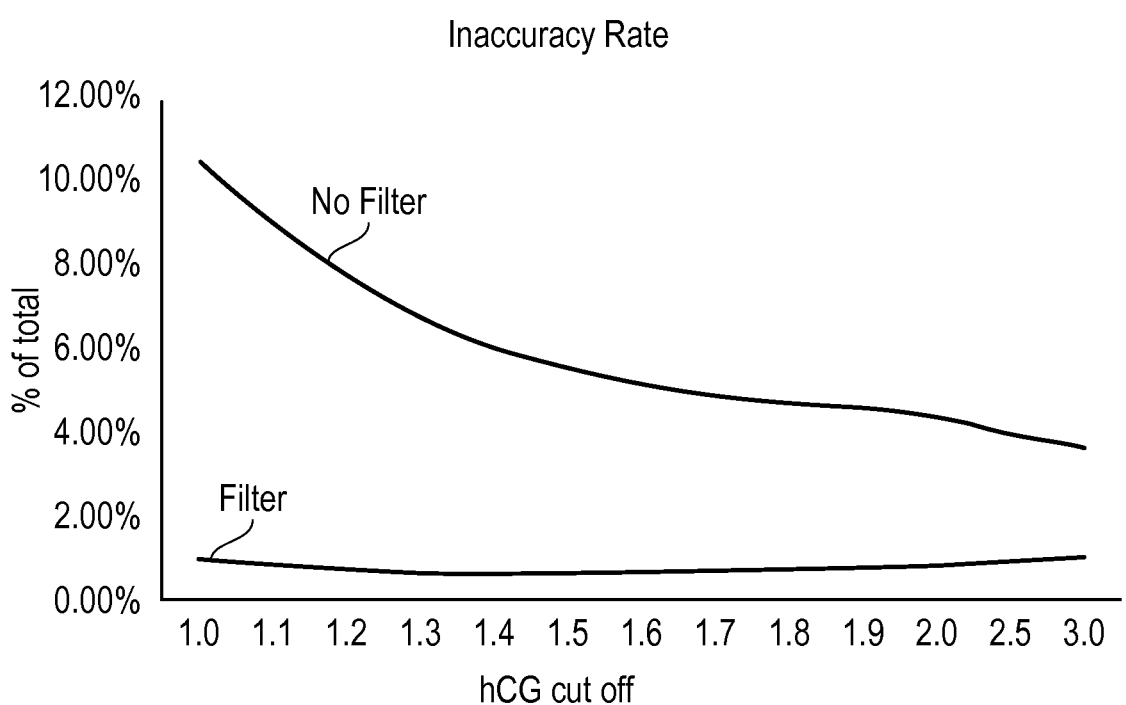
FIG. 15 provides a graph of inaccuracy rate based on the data of FIGS. 14A and 14B.

An inaccuracy rate (i.e. percentage at which any false result was predicted) is also represented graphically in FIG. 15. As can be seen, an approximately 10 fold improvement in accuracy of testing is achieved by applying filtering based on an LH threshold level of about 20 IU/L. Benefits were also seen at various other LH thresholds (e.g., at LH levels between 10 and 30 IU/L, 15 and 25 IU/L and 18 and 22 IU/L, etc.).

The experimental example illustrates the dynamic relationship between test accuracy and hCG and LH threshold levels. The experimental example shows that, when applying the LH filtering, where the false positive rate is desired to be no greater than e.g., 0.1% and/or when overall inaccuracy rate is desired to be as low as possible, an hCG threshold of about 1.0 to 2.0 IU/L, or about 1.3 to 1.9 IU/L, or about 1.3 to 1.8 IU/L, or about 1.3 to 1.7 IU/L or about 1.4 to 1.6 IU/L or about 1.5 IU/L, is advantageous. Nevertheless, considerable advantages can still be achieved using hCG threshold values outside of these ranges, in comparison to techniques that do not apply LH filtering at all.

Figure 16:
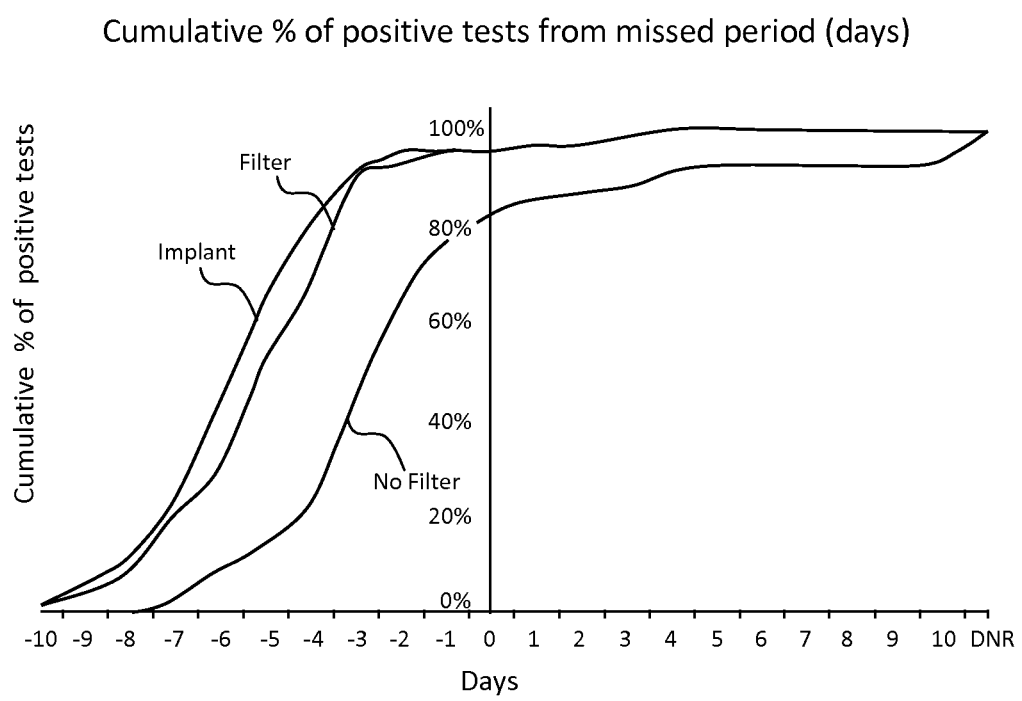
FIG. 16 provides a graph showing the cumulative percentage of accurate positive test results, identified over time relative to the first day that a period was missed, based on the sample data of the experimental example when LH filtering is applied and is not applied.

FIG. 16 provides a graph showing the cumulative percentage of accurate positive test results, identified over time relative to the first day that a period was missed, when pregnancy is determined when LH filtering is applied (LH threshold of about 20 IU/L and hCG threshold of about 1.5 IU/L) and when no LH filtering is applied (hCG threshold of about 20 IU/L). An illustrative model of pregnancy based on implantation ("implant') is also identified on the graph. As can be seen in FIG. 16, using the traditional pregnancy test technique that has no LH filter, approximately 50% of the total pregnancies were correctly identified at between two and three days before the missed period. On the other hand, when the hCG threshold is lowered in conjunction with LH filtering, 50% of the total pregnancies were correctly identified at approximately five days before the missed period.

The experimental example indicates not only that greater testing accuracy can be achieved by applying filtering based on measured and threshold LH levels, but that identification of pregnancy at an accuracy level equal to or exceeding current standards can be achieved based on much lower levels of measured hCG. This in turn means that earlier identification of pregnancy may be made. For example, whereas the accuracy of current tests (which measure hCG only and determine pregnancy based on hCG measurements>20 IU/L only) may achieve an acceptable positive test accuracy at an average of about 3 days from implantation, if optimum LH filtering is applied to the sample data acquired in this example, it has been determined that a corresponding degree of positive test accuracy can be achieved as early as about 0.5 days from implantation. This provides an improvement in early-testing capability following implantation of about 2.5 days.

It will be appreciated by persons skilled in the art that numerous variations and/or modifications may be made to the above-described embodiments, without departing from the broad general scope of the present disclosure. For example, while various threshold levels for testing hCG and TNT, etc., are provided, alternative threshold levels may be used. For example, the levels may be changed to achieve a more desirable balance between producing a sensitive test and eliminating the possibility of physiological noise affecting the accuracy of the test. Furthermore, the levels may be varied depending on changes in diagnostic practices in the medical industry or legal requirements. While embodiments of test devices for receiving urine and blood samples are described, the test devices may be adapted for receiving other types of samples. Furthermore, while embodiments of test devices that employ lateral flow test strips are described, other assays may be used, such as microfluidic devices including lab-on-a-chip (LOC) devices and other types of immunoassays and nucleic acid assays, for example. The present embodiments are, therefore, to be considered in all respects as illustrative and not restrictive.

The invention claimed is:

1. A pregnancy test device for identifying pregnancy in a human or animal body based on a biological sample obtained from the human or animal body, the test device comprising:
   a lateral flow test strip comprising one or more test portions configured to bind:
      human chorionic gonadotropin (hCG), when present, in the biological sample; and
      luteinizing hormone (LH), when present, in the biological sample; and
   a reader that analyses the one or more test portions and determines a level of hCG in the biological sample based on an amount of hCG bound at the one or more test portions and determines a level of LH in the biological sample based on an amount of LH bound at the one or more test portions, wherein the reader comprises a processor and a non-transitory computer-readable memory medium, the non-transitory computer-readable memory medium comprising instructions that cause the processor to:
   determine which of a plurality of discrete LH ranges the determined level of LH falls within, wherein the processor associates a different hCG threshold level with each one of the LH ranges,
   wherein the plurality of discrete LH ranges comprises a first LH range below a first LH threshold level and a second LH range above the first LH threshold level, the first LH threshold level being between 10 and 30 IU/L,
   wherein a first hCG threshold level of between 1.0 and 3.0 IU/L is associated with the first LH range; and a second hCG threshold level that is at least 2.0 IU/L greater than the first hCG threshold is associated with the second LH range;
   select the hCG threshold level that is associated with the LH range which the determined level of LH falls within; and
   identify pregnancy in the body if the determined level of hCG is above the selected hCG threshold level.

2. The pregnancy test device of claim 1, wherein the first LH range includes all LH values below the first LH threshold level, and the second LH range includes all LH values above the first LH threshold level.

3. The pregnancy test device of claim 1, wherein the first hCG threshold level is between 1.0 and 2.0 IU/L.

4. The pregnancy test device of claim 1, wherein the first hCG threshold level is between 1.3 and 1.9 IU/L.

5. The pregnancy test device of claim 1, wherein the first hCG threshold level is between 1.3 and 1.8 IU/L.

6. The pregnancy test device of claim 1, wherein the first hCG threshold level is between 1.3 and 1.7 IU/L.

7. The pregnancy test device of claim 1, wherein the first hCG threshold level is between 1.4 and 1.6 IU/L.

8. The pregnancy test device of claim 1, wherein the first hCG threshold level is about 1.5 IU/L.

9. The pregnancy test device of claim 1, wherein the difference between the first and second hCG threshold levels is at least 5 IU/L.

10. The pregnancy test device of claim 1, wherein the difference between the first and second hCG threshold levels is at least 10 IU/L.

11. The pregnancy test device of claim 1, wherein the difference between the first and second hCG threshold levels is at least 15 IU/L.

12. The pregnancy test device of claim 1, wherein the first LH threshold level is greater than 15 IU/L.

13. The pregnancy test device of claim 1, wherein the first LH threshold level is about 20 IU/L.

14. The pregnancy test device of claim 1, wherein: the first LH threshold level is greater than 15 IU/L; and the first hCG threshold level is between 1.4 and 2.0 IU/L.

15. The pregnancy test device of claim 1, wherein: the first LH threshold level is about 20 IU/L; and the first hCG threshold level is about 1.5 IU/L.

16. The pregnancy test device of claim 1, wherein the plurality of discrete LH ranges comprises a third LH range defined by a second LH threshold level, the second LH threshold level being higher than the first LH threshold level; wherein: the second LH range includes all LH values between the first LH threshold level and the second LH threshold level; and the third LH range includes all LH values above the second LH threshold level; and wherein: a third hCG threshold level is associated with the third LH range.

17. The pregnancy test device of claim 1, wherein the one or more test portions comprise one or more capture agents configured to specifically bind hCG, when present, in the biological sample, and LH, when present, in the biological sample.

18. The pregnancy test device of claim 16, wherein the first hCG threshold level is between 1.0 and 2.0 IU/L.

19. The pregnancy test device of claim 16, wherein the first hCG threshold level is between 1.3 and 1.9 IU/L.

20. The pregnancy test device of claim 16, wherein the first hCG threshold level is between 1.3 and 1.8 IU/L.

21. The pregnancy test device of claim 16, wherein the first hCG threshold level is between 1.3 and 1.7 IU/L.

22. The pregnancy test device of claim 16, wherein the first hCG threshold level is between 1.4 and 1.6 IU/L.

23. The pregnancy test device of claim 16, wherein the first hCG threshold level is about 1.5 IU/L.

24. The pregnancy test device of claim 16, wherein the difference between the first and second hCG threshold levels is at least 3 IU/L.

25. The pregnancy test device of claim 16, wherein the difference between the first and second hCG threshold levels is at least 5 IU/L.

26. The pregnancy test device of claim 16, wherein the difference between the second and third hCG threshold levels is at least 5 IU/L.

27. The pregnancy test device of claim 16, wherein the difference between the second and third hCG threshold levels is at least 10 IU/L.

28. The pregnancy test device of claim 16, wherein the difference between the second and third hCG threshold levels is at least 15 IU/L.

29. The pregnancy test device of claim 16, wherein the first LH threshold level is greater than 15 IU/L.

30. The pregnancy test device of claim 16, wherein the first LH threshold level is about 15 IU/L.

31. The pregnancy test device of claim 16, wherein the second LH threshold level is greater than 20 IU/L.

32. The pregnancy test device of claim 16, wherein the second LH threshold level is greater than 25 IU/L.

33. The pregnancy test device of claim 16, wherein the second LH threshold level is greater than 30 IU/L.

34. The pregnancy test device of claim 16, wherein the second LH threshold level is about 30 IU/L.

35. The pregnancy test device of claim 16, wherein: the first LH threshold level is between 10 IU/L and 20 IU/L; and the second LH threshold level is between 20 IU/L and 40 IU/L.

36. The pregnancy test device of claim 16, wherein: the first LH threshold level is between 10 IU/L and 20 IU/L; the second LH threshold level is between 20 IU/L and 40 IU/L; the second hCG threshold level is between 5 and 10 IU/L; and the third hCG threshold level is at least 20 IU/L.

37. The pregnancy test device of claim 16, wherein: the first LH threshold level is about 15 IU/L; the second LH threshold level is about 30 IU/L; the first hCG threshold level is about 1.5 IU/L the second hCG threshold level is about 5 IU/L; and the third hCG threshold level is about 20 IU/L.

* * * * *